(12) United States Patent
Stern et al.

(10) Patent No.: US 7,452,544 B2
(45) Date of Patent: Nov. 18, 2008

(54) BACTERIOCINS AND NOVEL BACTERIAL STRAINS

(75) Inventors: Norman J. Stern, Athens, GA (US);
Edward A. Svetoch, Serpukhov District (RU); Boris V. Eruslanov, Serpukhov District (RU); Larisa I. Volodina, Serpukhov District (RU); Yuri N. Kovalev, Serpukhov District (RU); Tamara Y. Kudryavtseva, Serpukhov District (RU); Vladimir V. Perelygin, Serpukhov District (RU); Victor D. Pokhilenko, Serpukhov District (RU); Vladimir P. Levchuk, Serpukhov District (RU); Valery N. Borzenkov, Serpukhov District (RU); Olga E. Svetoch, Serpukhov District (RU); Eugeni V. Mitsevich, Serpukhov District (RU); Irina P. Mitsevich, Serpukhov District (RU)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 11/499,225

(22) Filed: Aug. 4, 2006

(65) Prior Publication Data
US 2006/0269523 A1 Nov. 30, 2006

Related U.S. Application Data

(62) Division of application No. 10/644,927, filed on Aug. 21, 2003, now Pat. No. 7,132,102.

(51) Int. Cl.
*A61K 45/00* (2006.01)
*A61K 39/02* (2006.01)
*A61K 39/00* (2006.01)
*A01N 63/00* (2006.01)
*C07K 1/00* (2006.01)

(52) U.S. Cl. ............. 424/282.1; 424/278.1; 424/190.1; 424/93.45; 424/184.1; 424/93.1; 530/350

(58) Field of Classification Search ............. 424/190.1, 424/93.45, 93.1, 282.1, 184.1, 278.1; 530/300
See application file for complete search history.

(56) References Cited

U.S. PATENT DOCUMENTS 5,733,568 A 3/1998 Ford
6,403,082 B1 6/2002 Stiles et al.

OTHER PUBLICATIONS

Diep et al (Applied and Environmental Microbiology, 1994; 60(1): 160-166).*

Joosten, H., et al., "Purification and Characterization of Enterocin 4, a Bacteriocin Produced by *Enterococcus feccalis* INIA 4", *Applied and Environmental Microbiology*, vol. 62 (11), pp. 4220-4223, Nov. 1996.

Maisnier-Patin, S., et al., "Purification, Partial Characterisation and Mode of Action of Enterococcin EFS2, an Antilisterial Bacteriocin Produced by a Strain of *Enterococcus faecalis* Isolated from a Cheese", *International Journal of Food Microbiology*, vol. 30, pp. 255-270, 1996.

Balla, E., et al., "Characterization and Cloning of the Genes Encoding Enterocin 1071A and Enterocin 1071B, Two Antimicrobial Peptides Produced by *Enterococcus faecalis* BFE 1071", *Applied and Environ. Micro.*, vol. 66, (4), pp. 1298-1304, Apr. 2000.

Franz, C., et al., "Biochemical and Genetic Characterization of the Two-Peptide Bacteriocin Enterocin 1071 Produced by *Enterococcus faecalis* FAIR-E 309", *Applied and Environmental Microbiology*, vol. 68, (5), pp. 2550-2554, May 2002.

Nilsen, T., et al., "Enterolysin A, a Cell Wall-Degrading Bacteriocin from *Enterococcus faecalis* LMG 2333", *Applied and Environmental Microbiology*, vol. 69, (5), pp. 2975-2984, May 2003.

Guyonnet, D., et al., "Method for Rapid Purification of Class IIa Bacteriocins and Comparison of Their Activities", *Applied and Environmental Microbiology*, vol. 66, (4), pp. 1744-1748, Apr. 2000.

Juven, B., et al., "Antagonistic effects of lactobacilli and pediococci to control intestinal colonization by human enteropathogens in live poultry", *Journal of Applied Bacteriology*, vol. 70, pp. 95-103, 1991.

Moreno, M., et al., "Isolation and biochemical characterisation of enterocins produced by enterococci from different sources", Abstract—*Journal of Applied Microbiology*, vol. 94, (2), p. 214, Feb. 2003, abstract only.

Laukova, A., et al., "Occurrence of bacteriocin production among environmental entrococci", Medline Abstract—*Lett Appl Microbiol*, vol. 27, (3), pp. 178-182, Sep. 1, 1998, abstract only.

Lopez-Lara, I., et al., "Purification, characterization, and biological effects of a second bacteriocin from *Enterococcus faecalis* ssp. liquefaciens S-48 and it mutant strain B-48-28", Medline Abstract—*Can J Microbiol*, vol. 37, (10), pp. 769-774, Oct. 1, 1991, abstract only.

Nunez, M., et al., "Inhibition of Listeria monocytogenes by enterocin 4 during the manufacture and ripening of Manchego cheese", Medline Abstract—*J Appl Microbiol*, vol. 83, (6), pp. 671-677, Dec. 1, 1997, abstract only.

Rodriguez, E., et al., "Combined effect of bacteriocin-producing lactic acid bacteria and lactoperoxidase system activation on Listeria monocytogenes in refrigerated raw milk", Medline Abstract—*J Appl Microbiol*, vol. 83, (3), pp. 389-395, Sep. 1, 1997, abstract only.

(Continued)

*Primary Examiner*—Robert A Zeman
*Assistant Examiner*—Lakia J Tongue
(74) *Attorney, Agent, or Firm*—John Fado; Gail E. Poulos

(57) ABSTRACT

Novel bacteriocins and/or the novel lactic acid-producing strains are used for at least reducing the levels of colonization by at least one target bacteria in animals, especially poultry.

2 Claims, 3 Drawing Sheets

OTHER PUBLICATIONS

Jett, B., et al., "The growth-inhibitory effect of the *Enterococcus faecalis* bacteriocin encoded by pAD1 extends to the oral streptococci", Article, *Journal of Dental Research*, vol. 69, pp. 1640-1645, 1990, abstract only.

Du Toit, M., et al., "Preliminary characterization of bacteriocins produced by *Enterococcus faecium* and *Enterococcus faecalis* isolated from pig feces", Abstract, *Journal of Applied Microbiology*, vol. 88, (3), p. 482, Mar. 2000, abstract only.

Marekova, M., et al., "Partial characterization of bacteriocins produced by environmental strain *Enterococcus faecium* EK13", Abstract, *Journal of Applied Microbiology*, vol. 94, (3), p. 523, Mar. 2003, abstract only.

Simonetta, A., et al., "Antibacterial activity of enterococci strains against *Vibrio cholerae*", Medline Abstract, *Lett Appl Microbiol*, vol. 24, (2), pp. 139-143, Feb. 1, 1997, abstract only.

Lasagno, M., et al., "Selection of bacteriocin producer strains of lactic acid bacteria from a dairy environment", Medline Abstract, *New Microbiol*, vol. 25, (1), pp. 37-44, Jan. 1, 2002, abstract only.

Del Campo, R., et al., "Bacteriocin Production in Vancomycin-Resistant and Vancomycin-Susceptible *Enterococcus* Isolates of Different Origins", Abstract, *Antimicrobial Agents and Chemotherapy*, vol. 45, (3), pp. 905-912, Mar. 2001.

Galvez, A., et al., "Isolation and characterization of enterocin EJ97, a bacteriocin produced by *Enterococcus faecalis* EJ97", Abstract, *Arch Microbiol*, vol. 171, pp. 59-65, 1998.

Eguchi, T., "Isolation and characterization of enterocin SE-K4 produced by thermophilic enterococci, *Enterococcus faecalis* K-4", Medline Abstract, *Biosci Biotechnol Biochem*, vol. 65, (2), pp. 247-253, Feb. 1, 2001, abstract only.

Lopez-Lara, I., et al., "Purification, characterization, and biological effects of a second bacteriocin from *Enterococcus faecalis* ssp. liquefaciens S-48 and its mutant strain B-48-28", Medline Abstract, *Can J Microbiol*, vol. 37, (10), pp. 769-774, Oct. 1, 1991, abstract only.

Salzano, G., et al., "Conjugal transfer of plasmid-borne bacteriocin production in *Enterococcus faecalis* 226 NWC", *FEMS Microbiol Lett*, vol. 78, (1), pp. 1-6, Nov. 15, 1992, abstract only.

Elotmani, F., et al., "Characterization of anti-Listeria monocytogenes bacteriocins from *Enterococcus faecalis, Enterococcus faecium*, and *Lactococcus lactis* strains isolated from Ra?b, a Moroccan traditional fermented milk", *Curr Microbiol*, vol. 44, (1), pp. 10-17, Jan. 1, 2002, abstract only.

\* cited by examiner 1 2 3 4

1 2 3 4

1 2 3

SEQUENCE LISTING

<160> NUMBER OF SEQ ID NOS: 5

<210> SEQ ID NO 1
<211> LENGTH: 54
<212> TYPE: PRT
<213> ORGANISM: Lactobacillus salivarius

<400> SEQUENCE: 1

Lys Thr Tyr Tyr Gly Thr Asn Gly Val His Cys Thr Lys Asn Ser Leu
1               5                   10                  15

Trp Gly Lys Val Arg Leu Lys Asn Met Lys Tyr Asp Gln Asn Thr Thr
            20                  25                  30

Tyr Met Gly Arg Leu Gln Asp Ile Leu Leu Gly Trp Ala Thr Gly Ala
        35                  40                  45

```
Phe Gly Lys Thr Phe His
    50

<210> SEQ ID NO 2
<211> LENGTH: 56
<212> TYPE: PRT
<213> ORGANISM: Lactobacillus acidophilus

<400> SEQUENCE: 2

Ala Arg Lys Tyr Gly Asn Gly Val Cys Gly Ser Lys Trp Ile Asn Asn
1               5                   10                  15

Gly Gly Phe Gln Val Ile Gly Asn Asn Ala Ala Ala Asn Leu Thr Asn
            20                  25                  30

Trp Gly Glu Ala Phe Ala Ser Ala Thr Lys Ser Gly Cys Ser Ala Thr
        35                  40                  45

Thr Cys Ile Ile Asn Ala Met Ala
    50                  55

<210> SEQ ID NO 3
<211> LENGTH: 29
<212> TYPE: PRT
<213> ORGANISM: Enterococcus faecalis

<400> SEQUENCE: 3

Phe Asn Ile Arg Gly Gly Tyr Asn Phe Gly Lys Ser Val Arg His Val
1               5                   10                  15

Val Asp Ala Ile Gly Asn Met Ala Gly Ile Ile Lys Leu
            20                  25

<210> SEQ ID NO 4
<211> LENGTH: 49
<212> TYPE: PRT
<213> ORGANISM: Enterococcus faecalis

<400> SEQUENCE: 4

Val Phe His Ala Tyr Ser Ala Arg Gly Val Arg Asn Asn Tyr Lys Cys
1               5                   10                  15

Ala Gly Val Pro Asp Ala Ile Gly Cys Ala Val Arg Gly Ile Phe Ile
            20                  25                  30

His Gly Tyr Ser Leu Gln Trp Met Gln Val Lys Trp Gly Trp Leu Phe
        35                  40                  45

Lys

<210> SEQ ID NO 5
<211> LENGTH: 31
<212> TYPE: PRT
<213> ORGANISM: Enterococcus durans

<400> SEQUENCE: 5

Thr Lys Thr Thr Arg Gly Asn Gly Val Asn Lys Glu Cys Trp Glu Thr
1               5                   10                  15

Tyr Lys Ala Gly Thr Val Asp Ile Leu Trp Ala Ser Trp Ser Lys
            20                  25                  30
```

BACTERIOCINS AND NOVEL BACTERIAL STRAINS

This is a divisional of application Ser. No. 10/644,927 filed Aug. 21, 2003, which is herein incorporated by reference in its entirety.

BACKGROUND OF THE INVENTION

1. Field of the Invention

This invention relates to the control of disease in animals, especially poultry, through the use of novel bacteriocin-producing lactic acid-producing bacteria and/or novel bacteriocins produced by these species. It also relates to novel bacteriocins, amino acid sequences of the novel bacteriocins, and to the strains of lactic acid producing bacteria producing the novel bacteriocins. Furthermore, the invention relates to therapeutic compositions containing the novel bacteriocins and/or the strains of lactic acid producing bacteria producing them and to uses of the therapeutic compositions.

2. Description of the Related Art

The consumption of improperly prepared poultry products has resulted in human intestinal diseases. It has long been recognized that *Salmonella* spp. are causative agents of such diseases and more recently, *Campylobacter* spp., especially *Campylobacter jejuni*, has also been implicated. Both microorganisms may colonize poultry gastrointestinal tracts without any deleterious effects on the birds, and although some colonized birds can be detected, asymptomatic carriers can freely spread the microorganisms during production and processing, resulting in further contamination of both live birds and carcasses. Poultry serves as the primary reservoir for *Salmonella* and *Campylobacter* in the food supply (Jones et al., Journal of Food Protection, Volume 54, No. 7, 502-507, July, 1991). Prevention of colonization in live poultry during growout production may diminish the problem of poultry contamination.

A number of factors contribute to the colonization and continued presence of bacteria within the digestive tract of animals. These factors have been extensively reviewed by Savage (Progress in Food and Nutrition Science, Volume 7, 65-74, 1983). Included among these factors are : (1) Gastric acidity (Gilliland, Journal of Food Production, Volume 42, 164-167, 1979); (2) bile salts (Sharpe & Mattick, Milchwissenschaft, Volume 12, 348-349, 1967; Floch et al., American Journal of Clinical Nutrition, Volume 25, 1418-1426, 1972; Lewis & Gorbach, Archives of Internal Medicine, Volume 130, 545-549, 1972; Gilliland and Speck, Journal of Food Protection, Volume 40, 820-823, 1977); Hugdahl et al., Infection and Immunity, Volume 56, 1560-1566, 1988); (3) peristalsis; (4) digestive enzymes (Marmur, Journal of Molecular Biology, Volume 3, 208-218, 1961); (5) immune response; and (6) indigenous microorganisms and the antibacterial compounds which they produce. The first four factors are dependent on the phenotype of the host and may not be practically controllable variables. The immune response in the gastrointestinal (GI) tract is not easily modulated. The factors involving indigenous microorganisms and their metabolites are dependent on the normal flora of the GI tract.

One potential approach to control *Campylobacter* and/or *Salmonella* colonization is through the use of competitive exclusion (CE). Nurmi and Rantala (Nature, Volume 241, 210-211, 1973) demonstrated effective control of *Salmonella* infection by gavaging bacteria from healthy poultry intestinal materials into young chicks whose microflora had not yet been established, against *Salmonella* colonization. Administration of undefined CE preparations to chicks speeds the maturation of gut flora in newly-hatched birds and provides a substitute for the natural process of transmission of microflora from the adult hen to its offspring. Results from laboratory and field investigations provide evidence of benefits in *Campylobacter* control through administering normal microflora to chickens; decreased frequency of *Campylobacter*-infected flocks (Mulder and Bolder, IN: Colonization Control of human bacterial enteropathogens in poultry; L. C. Blankenship (ed.), Academic Press, San Diego, Calif., 359-363, 1991) and reduced levels of *Campylobacter jejuni* (*C. jejuni*) in the feces of colonized birds has been reported (Stern, Poultry Science, Volume 73, 402-407, 1994).

Schoeni and Wong (Appl. Environ. Microbiol., Volume 60, 1191-1197, 1994) reported a significant reduction in broiler colonization by *C. jejuni* through the application of carbohydrate supplements together with three identified antagonists: *Citrobacter diversus* 22, *Klebsiella pneumoniae* 23, and *Escherichia coli* 25. There is also evidence of a significant decrease of *C. jejuni* in intestinal samples from infected broilers after treatment with poultry-isolated cultures of *Lactobacillus acidophilus* and *Streptococcus faecium* (Morishita et al., Avian Diseases, Volume 41, 850-855, 1997).

Snoeyenbos et al. (U.S. Pat. No. 4,335,107, June, 1982) developed a competitive exclusion (CE) microflora technique for preventing *Salmonella* colonization by lyophilizing fecal droppings and culturing this preparation anaerobically. Mikola et al. (U.S. Pat. No. 4,657,762, April, 1987) used intestinal fecal and cecal contents as a source of CE microflora for preventing *Salmonella* colonization. Stern et al. (U.S. Pat. No. 5,451,400, September, 1995 and U.S. Pat. No. 6,241, 335, April 2001) disclose a mucosal CE composition for protection of poultry and livestock against colonizations by *Salmonella* and *Campylobacter* where the mucin layer of prewashed caeca is scraped and the scrapings, kept in an oxygen-free environment, are cultured anaerobically. Nisbet et al. (U.S. Pat. No. 5,478,557, December, 1996) disclose a defined probiotic that can be obtained from a variety of domestic animals which is obtained by continuous culture of a batch culture produced directly from fecal droppings, cecal and/or large intestine contents of the adult target animal.

Microorganisms produce a variety of compounds which demonstrate anti-bacterial properties. One group of these compounds, the bacteriocins, consists of bactericidal proteins with a mechanism of action similar to ionophore antibiotics. Bacteriocins are often active against species which are closely related to the producer. Their widespread occurrence in bacterial species isolated from complex microbial communities such as the intestinal tract, the oral or other epithelial surfaces, suggests that bacteriocins may have a regulatory role in terms of population dynamics within bacterial ecosystems. Bacteriocins are defined as compounds produced by bacteria that have a biologically active protein moiety and bactericidal action (Tagg et al., Bacteriological Reviews, Volume 40, 722-256, 1976). Other characteristics may include: (1) a narrow inhibitory spectrum of activity centered about closely related species; (2) attachment to specific cell receptors; and (3) plasmid-borne genetic determinants of bacteriocin production and of host cell bacteriocin immunity. Incompletely defined antagonistic substances have been termed "bacteriocin-like substances". Some bacteriocins effective against Gram-positive bacteria, in contrast to Gram-negative bacteria, have wider spectrum of activity. It has been suggested that the term bacteriocin, when used to describe inhibitory agents produced by Gram-positive bacteria, should meet the minimum criteria of (1) being a peptide and (2) possessing bactericidal activity (Tagg et al., supra).

Lactic acid bacteria are among the most important probiotic microorganisms. They are Gram-positive, nonsporing, catalase-negative organisms devoid of cytochromes. They are anaerobic but are aerotolerant, fastidious, acid-tolerant, and strictly fermentative with lactic acid as the major end-product of sugar fermentation. Lactic acid producing bacteria include *Lactobacillus* species, *Bifidobacterium* species, *Enterococcus faecalis*, *Enterococcus faecium*, *Lactococcus lactis*, *Leuconostoc mesenteroides*, *Pediococcus acidilactici*, *Sporolactobacillus inulinus*, *Streptococcus thermophilus*, etc. These species are of particular interest in terms of widespread occurrence of bacteriocins within the group and are also in wide use throughout the fermented dairy, food and meat processing industries. Their role in the preservation and flavour characteristics of foods has been well documented. Most of the bacteriocins produced by this group are active only against other lactic acid bacteria, but several display anti-bacterial activity towards more phylogenetically distant Gram-positive bacteria and, under certain conditions, Gram-negative bacteria.

*Lactobacilli* have been extensively studied for production of antagonists. These include the well characterized bacteriocins (DeKlerk, 1967; Upreti and Hinsdill 1975; Barefoot and Klaenhammer 1983; Joerger and Klaenhammer 1986); potential bacteriocin-like substances (Vincent et al., 1959), and other antagonists not necessarily related to bacteriocins (Vakil and Shahni 1965; Hamdan and Mikolajcik 1974; Mikolajcik and Hamdan 1975; and Shahni et al., 1976).

Klaenhammer (1993) has classified the lactic acid bacteria bacteriocins known to date into four major groups:

Class I-Lantibiotics which are small peptides of <5 kDa containing the unusual amino acids lanthionine and β-methyl lanthionine. These are of particular interest in that they have very broad spectra of activity relative to other bacteriocins. Examples include Nisin, Nisin Z, carnocin U 149, lacticin 481, and lactocin 5.

Class II-Small non-lanthionine containing peptides: a heterogeneous group of small peptides of <10 kDa. This group includes peptides active against *Listeria* spp.

Class III-Large heat labile proteins >30 kDa. An example is Helveticin.

Class IV-Complex bacteriocins-proteins containing additional moieties such as lipids and carbohydrates.

The present invention provides novel compositions containing at least one novel strain of a lactic acid-producing bacterial strain and/or novel bacteriocins produced by the at least one novel strain; a method of using the strain or bacteriocin, the novel strains, amino acid sequences for the novel bacteriocins, and methods of use, all of which are different from related art strains, bacteriocins, and methods of using.

SUMMARY OF THE INVENTION

It is therefore an object of the present invention to provide novel strains of *Lactobacillus* and *Enterococcus* that produce novel bacteriocins.

A further object of the present invention is to provide a novel *Lactobacillus salivarius* strain PVD32 having the identifying characteristics of NRRL B-30514.

A still further object of the present invention is to provide a novel *Lactobacillus acidophilus* LWP320 having the identifying characteristics of NRRL B-30510.

A still further object of the present invention is to provide a novel *Enterococcus faecalis* LWP21 having the identifying characteristics of NRRL B-30645.

A still further object of the present invention is to provide a novel *Enterococcus durans* strain LWP26 having the identifying characteristics of NRRL B-30511.

A further object of the present invention is to provide novel bacteriocins produced by novel strains of *Lactobacillus* and *Enterococcus*.

A still further object of the present invention is to provide a novel bacteriocin OR7 having an amino acid sequence as set forth in SEQ ID NO 1.

A still further object of the present invention is to provide a novel bacteriocin LWP320 having an amino acid sequence as set forth in SEQ ID NO 2.

A still further object of the present invention is to provide a novel bacteriocin LWP21 having an amino acid sequence as set forth in SEQ ID NO 3.

A still further object of the present invention is to provide a novel bacteriocin LWP26 having an amino acid sequence as set forth in SEQ ID NO 4.

Another object of the present invention is to provide a method for at least reducing the levels of colonization of at least one target bacteria in animals by administering to the animal a therapeutic composition including at least one novel strain of *Lactobacillus* or *Enterococcus* that produces a novel bacteriocin, at least one novel bacteriocin produced by a novel strain of *Lactobacillus* or *Enterococcus*, or a combination of the novel strains and/or novel bacteriocins.

A further object of the present invention is to provide a method for at least reducing levels of colonization by at least one target bacteria in animals by administering to the animal a therapeutic composition including a novel strain of *Lactobacillus* having the characteristics of NRRL Deposit No. B-30514 and B-30510; *Enterococcus* having the identifying characteristics of NRRL B-30511 and NRRL B-30645; and mixtures thereof.

A still further object of the present invention is to provide a method for at least reducing the levels of colonization of at least one target bacteria in animals by administering to the animal a therapeutic composition including at least one novel strain with the identifying characteristics of NRRL B-30510, NRRL B-30511, NRRL 30514, NRRL B-30645, and mixtures thereof; at least one novel bacteriocin having an amino acid sequence as set forth in SEQ ID NO 1, SEQ ID NO 2, SEQ ID NO 3, SEQ ID NO 4, and mixtures thereof; or a combination of novel strains and novel bacteriocins.

A still further object of the present invention is to provide a method for at least reducing the levels of colonization by at least one target bacteria in animals by administering to the animal a therapeutic composition including a novel bacteriocin having an amino acid sequence as set forth in SEQ ID NO 1.

A still further object of the present invention is to provide a method for at least reducing the levels of colonization by at least on target bacteria in animals by administering to the animal a therapeutic composition including a novel bacteriocin having an amino acid sequence as set forth in SEQ ID NO 2.

A still further object of the present invention is to provide a method for at least reducing the levels of colonization by at least on target bacteria in animals by administering to the animal a therapeutic composition including a novel bacteriocin having an amino acid sequence as set forth in SEQ ID NO 3.

A still further object of the present invention is to provide a method for at least reducing the levels of colonization by at least one target bacteria in animals by administering to the animal a therapeutic composition including a novel bacteriocin having an amino acid sequence as set forth in SEQ ID NO 4.

Another object of the present invention is to provide a method for at least reducing the levels of colonization by at least one target bacteria in an animal by administering to the animal a therapeutic composition comprising a bacteriocin produced by a novel strain of a *Lactobacillus* bacteria having the identifying characteristics of NRRL B-30510 or NRRL B-30514; a novel strain of *Enterococcus* having the identifying characteristics of NRRL B-30511 or NRRL B-30645, and mixtures thereof.

Further objects and advantages of the invention will become apparent from the following description.

Deposit of the Microorganisms

*Lactobacillus salivarius*, designated NRRL B-30514 (Strain PVD32), *Lactobacillus acidophilus* designated NRRL B-30510 (Strain LWP320; *Enterococcus durans* designated NRRL B-30511 (Strain LWP26)were deposited on Aug. 3, 2001 and *Enterococcus faecalis* designated NRRL B-30645 (Strain LWP21), was deposited on Apr. 1, 2003. All of the above strains have been deposited under the provisions of the Budapest Treaty, with the U.S.D.A. Agricultural Research Service Patent Culture Collection (National Center for Agricultural Utilization Research, 1815 N. University Street, Peoria, Ill. 61604).

DETAILED DESCRIPTION OF THE INVENTION

Figure 1:
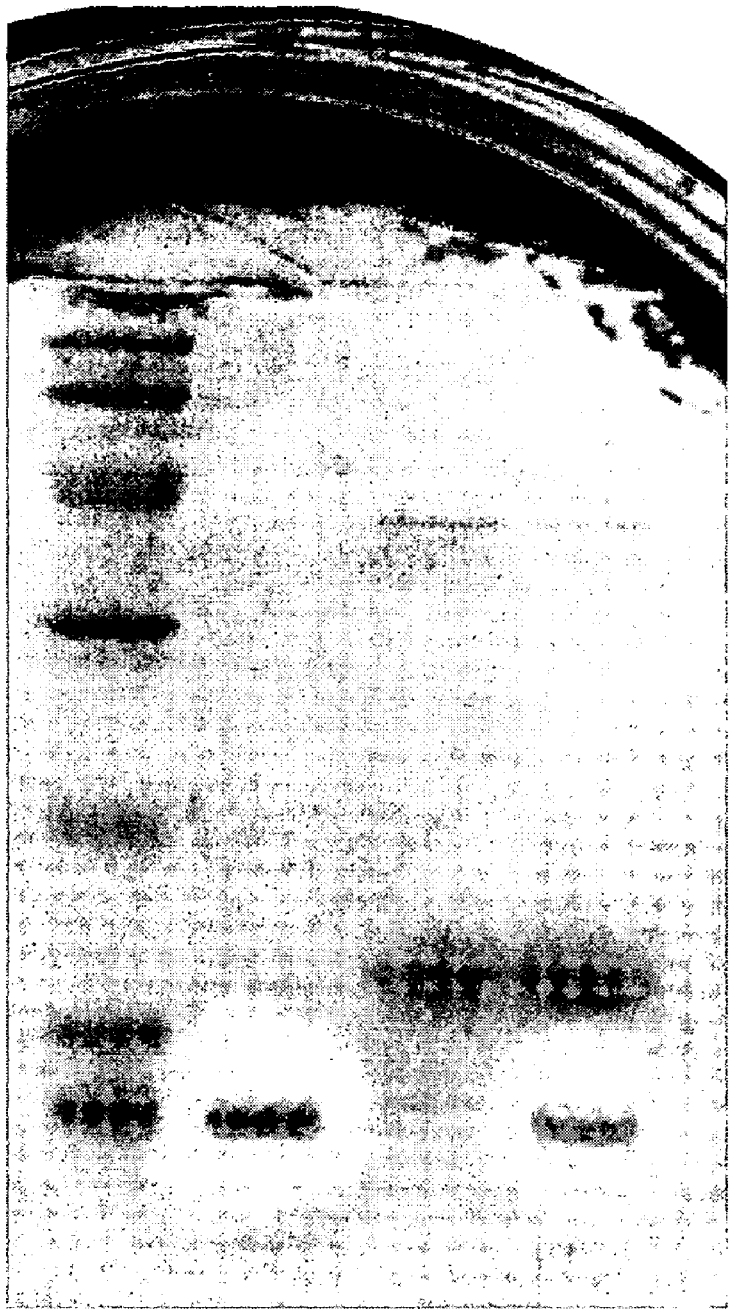
FIG. 1 is a photograph showing direct detection of OR7 after SDS-PAGE. The gel was overlaid with *Campylobacter jejuni* to determine which band(s) correspond to antimicrobial activity and the molecular weight of the band with activity. Lane 1—Molecular Weight Markers MMW Range 6,500-97,000 (AMERSHAM PHARMACIA BIOTECH): 97,000, 66,000, 43,000, 30,000, 21,000, 14,400, and 6,500 Da. The band in lane 2—pure lactocin OR7, the band in lane 3—CAP lactocin OR7 following absorption by *C. jejuni*, which corresponds to the antimicrobial activity, the zone of growth inhibition (see arrow), had a mass of about 6,000 Da, the band in lane 4—CAP lactocin OR7. Other bands did not show antimicrobial activity.

The importance of enteric infections in humans has been increasingly well recognized and the relationship of poultry contamination and human infection is well documented. The ability to diminish this health hazard by interventions at poultry processing plants is also well known. During broiler production and processing, fecal materials containing pathogens are transferred onto meat and persist in the food processing kitchens.

Metabolites of competing organisms may contribute to the control of pathogens such as *Campylobacter jejuni* and *Salmonella*. The novel antagonistic strains of the present invention were isolated from cecal and crop mucosal surfaces of broilers. The native components of characterized antagonist are low molecular weight peptides, bacteriocins, which have a wide spectrum of antagonistic activity.

The present invention provides novel *Lactobacillus* and *Enterococcus* strains, novel bacteriocins, amino acid sequences of said bacteriocins, therapeutic compositions containing the novel bacteriocins and/or strains producing them, and methods for using the novel therapeutic compositions.

The *Lactobacillus acidophilus* LWP320 isolate is a facultative anaerobe (microaerophile), catalase-negative, Gram-positive nonmotile pleomorphic rods which has delayed growth on MRS agar at about 37° C. When grown on MRS agar, the isolate produces albescent, semiopaque colonies that are about 0.5 mm to about 0.8 mm in diameter after about a 24 hour microaerophile incubation. In MRS broth the strain LWP320 grows only at the bottom of a culture tube.

The *Lactobacillus salivarius* PVD32 strain is a facultative anaerobe (microaerophile), Gram-positive, catalase-negative, nonmotile, pleomorphic rods. The colonies produce circular to regular-shaped, smooth, convex colonies with sharp margins that are about 1 mm to about 3 mm in diameter after microaerophile incubation for about 18-24 hours at about 37° C. The strains produce lactic acid and $H_2O_2$.

The *Enterococcus faecalis* LWP21 strain is a factultative anaerobe (microaerophile), Gram-positive cocci, catalase negative. The growth is delayed on MRS agar at 37° C. When cultured on MRS agar, the strain produces albescent, semiopaque colonies that are about 0.2 mm in diameter after microaerophile incubation for about 24 hours at about 37° C. After about 48 hours microaerophile incubation at about 37° C., the colonies are about 1 mm to about 1.2 mm in diameter. The strain grows in MRS broth only in about ⅔ of the volume at the bottom of the culture tube.

The *Enterococcus durans* LWP26 strain is a facultative anaerobe (microaerophile), Gram-positive cocci, catalase negative with delayed growth on MRS agar at about 37° C. When grown on MRS agar, the strain produces albescent, semiopaque colonies that are opaque after about 24 hours of microaerophilic incubation at about 37° C. After about 48 hours of microaerophilic incubation at about 37° C., colony sizes average from about 0.8 mm to about 1.0 mm. In MRS broth, the strain grows into all volumes of the tube.

Screening of isolated *Lactobacillus* and *Enterococcus* species for the production of bacteriocin activity is performed on nutrient agar on cultures seeded with different target bacteria of interest. Other test strains are cultured under aerobic conditions at about 37° C. for about 14-24 hours. *Yersinia enterocolitica* and *Y. pseudotuberculosis* are cultured at about 28° C. under aerobic conditions for about 14-24 hours. Tests for activity against *Campylobacter jejuni* are performed on *C. jejuni* seeded *Campylobacter* agar containing about 5% lysed blood. The use of blood is well within the ordinary skill in the art and include for example, sheep, horse, etc. Tests for activity against *Campylobacter jejuni* is carried out under microaerobic conditions of about 5% $O_2$, about 10% $CO_2$, and about 85% $N_2$ for about 24-48 hours at about 42° C. Approximately 0.2 ml of the antagonistic bacteria suspended in normal saline is plated onto *Lactobacillus* agar and incubated for about 24 hours. Agar blocks of about 0.5 cm$^3$ are cut out and transferred onto brucella or *Campylobacter* agar supplemented with lysed blood, about 10 micrograms /ml rifampicin, about 2.4 U/ml of polymyxin, and seeded with about 10$^7$ cells of *Campylobacter jejuni*. Plates are incubated at about 42° C. for approximately 24-48 hours under microaerobic conditions. Activity is evaluated by measuring zones of growth inhibition.

*Lactobacillus* isolates found to be antagonistic are evaluated for bacteriocin production. Crude antimicrobial preparations (CAPs) are prepared by ammonium sulfate precipitation only from cultures of antagonistic strains grown on starvation medium:

| | |
|---|---|
| $K_2HPO_4$ | 6.0 grams |
| $KH_2PO_4$ | 0.2 gram |
| $(NH_4)_2SO_4$ | 0.2 gram |
| $MgSO_4$ | 0.1 gram |
| glucose | 9.0 grams |
| histidine | 0.08 gram |
| arginine | 0.02 gram |

Add distilled $H_2O$ to 1000 ml, pH about 7.2 at about 37° C. for about 18 hours under aerobic conditions. The culture fluids are then centrifuged at about 12,000×g for about 10 minutes. The resulting supernatants are then adjusted to pH of about 6.2 by adding 1N NaOH and about 130 U/ml catalase to remove organic acids and hydrogen peroxide, and inhibiting factors. Antagonistic peptides are isolated from supernatant by a combination of ammonium sulfate precipitation, desalting chromatography and gel filtration to produce a crude antimicrobial preparation (CAP). CAP samples are filtered through 0.22µ filters (Millipore, Bedford, Mass., USA).

*Enterococcus* isolates found to be antagonistic are evaluated for bacteriocin production. Crude antimicrobial preparations (CAPs) are prepared by ammonium sulfate precipitation only from cultures of antagonistic strains grown in MRS broth:

| | |
|---|---|
| MRS broth | 15.0 grams |
| Lactose | 0.05 gram |

Add distilled $H_2O$ to about 1000 ml, pH 7.2 at about 37° C. for about 18 hours under aerobic conditions. The culture fluids are then centrifuged at about 12,000×g for about 10 minutes. The resulting supernatants are then adjusted to pH of about 6.2 by adding 1N NaOH and about 130 U/ml catalase to remove organic acids and hydrogen peroxide, and inhibiting factors. Antagonistic peptides are isolated from supernatant by a combination of ammonium sulfate precipitation, desalting chromatography and gel filtration to produce a crude antimicrobial preparation (CAP). CAP samples are filtered through 0.22µ filters (Millipore, Bedford, Mass., USA).

Molecular weights of all of the peptides are determined by SDS-PAGE electrophoresis. pIs of the peptides are determined by isoelectric focusing. Amino acid sequences are determined by Edman degradation using, for example, a 491 cLC Automatic Sequencer (Applied Biosystems, Inc.).

For purposes of the present invention, the term "peptide" means a compound of at least two or more amino acids or amino acid analogs. The amino acids or amino acid analogs may be linked by peptide bonds. In another embodiment, the amino acids may be linked by other bonds, e.g., ester, ether, etc. Peptides can be in any structural configuration including linear, branched, or cyclic configurations. As used herein, the term "amino acids" refers to either natural or synthetic amino acids, including both the D or L optical isomers, and amino acid analogs.

Peptide derivatives and analogs of the present invention include, but are not limited to, those containing, as a primary amino acid sequence, all or part of the amino acid sequence of the peptide including altered sequences in which functionally equivalent amino acid residues are substituted for residues within the sequence resulting in conservative amino acid substitution.

For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan, and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic acid and glutamic acid. Such alterations will not be expected to significantly affect apparent molecular weight as determined by polyacrylamide gel electrophoresis or isoelectric point. Non-conservative amino acid substitutions may also be introduced to substitute an amino acid with a particularly preferable property. For example, Cys may be introduced at a potential site for disulfide bridges with another Cys. Pro may be introduced because of its particularly planar structure.

The peptides of the present invention can be chemically synthesized. Synthetic peptides can be prepared using the well known techniques of solid phase, liquid phase, or peptide condensation techniques, or any combination thereof, and can include natural and/or synthetic amino acids. Amino acids used for peptide synthesis may be standard Boc($N^\alpha$-amino protected $N^\alpha$-t-butyloxycarbonyl) amino acid resin with the standard deprotecting, neutralization, coupling, and wash protocols of the original solid phase procedure of Merrifield (J. Am. Chem. Soc., Volume 85, 2149-2154, 1963), or the base-labile $N^\alpha$-amino protected 9-fluorenylmethoxycarbonyl (Fmoc) amino acid (Carpino and Han, J. Org. Chem., Volume 37, 3403-3409, 1972). In addition, the method of the present invention can be used with other $N^\alpha$-protecting groups that are familiar to those skilled in the art. Solid phase peptide synthesis may be accomplished by techniques within the ordinary skill in the art (See for example Stewart and Young, Solid Phase Synthesis, Second Edition, Pierce Chemical Co., Rockford, Ill., 1984; Fields and Noble, Int. J. Pept. Protein Res., Volume 35, 161-214, 1990), or by using automated synthesizers.

In accordance with the present invention, the peptides and/or the novel bacterial strains can be administered in a therapeutically acceptable carrier topically, parenterally, transmucosally, such as for example, orally, nasally, or rectally, or transdermally. The peptides of the present invention can be modified if necessary to increase the ability of the peptide to cross cellular membranes such as by increasing the hydrophobic nature of the peptide, introducing the peptide as a conjugate to a carrier, such as a ligand to a specific receptor, etc.

The present invention also provides for conjugating a targeting molecule to a peptide of the invention. Targeting molecules for purposes of the present invention mean a molecule which when administered in vivo, localizes to a desired location or locations. In various embodiments of the present invention, the targeting molecule can be a peptide or protein, antibody, lectin, carbohydrate, or steroid. The targeting molecule can be a peptide ligand of a receptor on the target cell or an antibody such as a monoclonal antibody. To facilitate crosslinking the antibody can be reduced to two heavy and light chain heterodimers, or the $F(ab')_2$ fragment can be reduced, and crosslinked to the peptide via the reduced sulfhydryl.

Another aspect of the present invention is to provide therapeutic compositions. The compositions may be for oral, nasal, pulmonary administration, injection, etc. The therapeutic compositions include effective amounts of at least one bacteriocin of the present invention and their derivatives and/or at least one novel strain to at least reduce the levels of colonization by at least one target bacteria together with acceptable diluents, preservatives, solubilizers, emulsifiers, adjuvants, and/or carriers. Diluents can include buffers such as Tris-HCl, acetate, phosphate, for example; additives can include detergents and solubilizing agents such as Tween 80, Polysorbate 80, etc., for example; antioxidants include, for example, ascorbic acid, sodium metabisulfite, etc.; preservatives can include, for example, Thimersol, benzyl alcohol, etc.; and bulking substances such as lactose, mannitol,etc.

The therapeutic composition of the present invention can be incorporated into particulate preparation of polymeric compounds such as polyvinylpyrrolidone, polylactic acid, polyglycolic acid, etc., or into liposomes. Liposomal encapsulation includes encapsulation by various polymers. A wide variety of polymeric carriers may be utilized to contain and/or deliver one or more of the therapeutic agents discussed above, including for example both biodegradable and nonbiodegradable compositions. Representative examples of biodegradable compositions include albumin, collagen, gelatin, hyaluronic acid, starch, cellulose (methylcellulose, hydroxypropylcellulose, hydroxypropylmethylcellulose, carboxymethylcellulose, cellulose acetate phthalate, cellulose acetate succinate, hydroxypropylmethylcellulose phthalate), casein, dextrans, polysaccharides, fibrinogen, poly(D,L lactide), poly (D,L-lactide-co-glycolide), poly(glycolide), poly(hydroxybutyrate), poly(alkylcarbonate) and poly (orthoesters), polyesters, poly(hydroxyvaleric acid), polydioxanone, poly(ethylene terephthalate), poly(malic acid), poly(tartronic acid), polyanhydrides, polyphosphazenes, poly(amino acids) and their copolymers (see generally, Illum, L., Davids, S. S. (eds.) "Polymers in Controlled Drug Delivery" Wright, Bristol, 1987; Arshady, J. Controlled Release 17:1-22, 1991; Pitt, Int. J. Phar. 59:173-196, 1990; Holland et al., J. Controlled Release 4:155-0180, 1986).

Representative examples of nondegradable polymers include poly(ethylene-vinyl acetate) ("EVA") copolymers, silicone rubber, acrylic polymers (polyacrylic acid, polymethylacrylic acid, polymethylmethacrylate, polyalkylcynoacrylate), polyethylene, polypropylene, polyamides (nylon 6,6), polyurethane, poly(ester urethanes), poly(ether urethanes), poly(ester-urea), polyethers (poly(ethylene oxide), poly(propylene oxide), Pluronics and poly(tetramethylene glycol)), silicone rubbers and vinyl polymers such as polyvinylpyrrolidone, poly(vinyl alcohol), poly(vinyl acetate phthalate) . Polymers may also be developed which are either anionic (e.g., alginate, carrageenin, carboxymethyl cellulose and poly(acrylic acid), or cationic (e.g., chitosan, poly-L-lysine, polyethylenimine, and poly (allyl amine)) (see generally, Dunn et al., J. Applied Polymer Sci. 50:353-365, 1993; Cascone et al., J. Materials Sci.: Materials in Medicine 5:770-774, 1994; Shiraishi et al., Biol. Pharm. Bull. 16(11) :1164-1168, 1993; Thacharodi and Rao, Int'l J. Pharm. 120:115-118, 1995; Miyazaki et al., Int'l J. Pharm. 118:257-263, 1995).

Polymeric carriers can be fashioned in a variety of forms, with desired release characteristics and/or with specific desired properties. For example, polymeric carriers may be fashioned to release a therapeutic agent upon exposure to a specific triggering event such as pH (see e.g., Heller et al., "Chemically Self-Regulated Drug Delivery Systems," in Polymers in Medicine III, Elsevier Science Publishers B. V., Amsterdam, 1988, pp. 175-188; Kang et al., J. Applied Polymer Sci. 48:343-354, 1993; Dong et al., J. Controlled Release 19:171-178, 1992; Dong and Hoffman, J. Controlled Release 15:141-152, 1991; Kim et al., J. Controlled Release 28:143-152, 1994; Cornejo-Bravo et al., J. Controlled Release 33:223-229, 1995; Wu and Lee, Pharm. Res. 10(10):1544-1547, 1993; Serres et al., Pharm. Res. 13(2):196-201, 1996; Peppas, "Fundamentals of pH- and Temperature-Sensitive Delivery Systems," in Gurny et al. (eds.), Pulsatile Drug Delivery, Wissenschaftliche Verlagsgesellschaft mbH, Stuttgart, 1993, pp. 41-55; Doelker, "Cellulose Derivatives," 1993, in Peppas and Langer (eds.), Biopolymers I, Springer-Verlag, Berlin). Representative examples of pH-sensitive polymers include poly(acrylic acid) and its derivatives (including for example, homopolymers such as poly(aminocarboxylic acid); poly (acrylic acid); poly (methyl acrylic acid), copolymers of such homopolymers, and copolymers of poly (acrylic acid) and acrylmonomers such as those discussed above. Other pH sensitive polymers include polysaccharides such as cellulose acetate phthalate; hydroxypropylmethylcellulose phthalate; hydroxypropylmethylcellulose acetate succinate; cellulose acetate trimellilate; and chitosan. Yet other pH sensitive polymers include any mixture of a pH sensitive polymer and a water soluble polymer.

Likewise, polymeric carriers can be fashioned which are temperature sensitive (see e.g., Chen et al., "Novel Hydrogels of a Temperature-Sensitive Pluronic Grafted to a Bioadhesive Polyacrylic Acid Backbone for Vaginal Drug Delivery," in Proceed. Intern. Symp. Control. Rel. Bioact. Mater. 22:167-168, Controlled Release Society, Inc., 1995; Okano, "Molecular Design of Stimuli-Responsive Hydrogels for Temporal Controlled Drug Delivery," in Proceed. Intern. Symp. Control. Rel. Bioact. Mater. 22:111-112, Controlled Release Society, Inc., 1995; Johnston et al., Pharm. Res. 9 (3) :425-433, 1992; Tung, Int'l J. Pharm. 107:85-90, 1994; Harsh and Gehrke, J. Controlled Release 17:175-186, 1991; Bae et al., Pharm. Res. 8(4):531-537, 1991; Dinarvand and D'Emanuele, J. Controlled Release 36:221-227, 1995; Yu and Grainger, "Novel Thermo-sensitive Amphiphilic Gels: Poly N-isopropylacrylamide-co-sodium acrylate-co-n-N-alkylacrylamide Network Synthesis and Physicochemical Characterization," Dept. of Chemical & Biological Sci., Oregon Graduate Institute of Science & Technology, Beaverton, Oreg., pp. 820-821; Zhou and Smid, "Physical Hydrogels of Associative Star Polymers," Polymer Research Institute, Dept. of Chemistry, College of Environmental Science and Forestry, State Univ. of New York, Syracuse, N.Y., pp. 822-823; Hoffman et al., "Characterizing Pore Sizes and Water Structure in Stimuli-Responsive Hydrogels," Center for Bioengineering, Univ. of Washington, Seattle, Wash., p. 828; Yu and Grainger, "Thermo-sensitive Swelling Behavior in Crosslinked N-isopropylacrylamide Networks: Cationic, Anionic and Ampholytic Hydrogels," Dept. of Chemical & Biological Sci., Oregon Graduate Institute of Science & Technology, Beaverton, Oreg., pp. 829-830; Kim et al., Pharm. Res. 9(3):283-290, 1992; Bae et al., Pharm. Res. 8(5):624-628, 1991; Kono et al., J. Controlled Release 30:69-75, 1994; Yoshida et al., J. Controlled Release 32:97-102, 1994; Okano et al., J. Controlled Release 36:125-133, 1995; Chun and Kim, J. Controlled Release 38:39-47, 1996; D'Emanuele and Dinarvand, Int'l J. Pharm. 118:237-242, 1995; Katono et al., J. Controlled Release 16:215-228, 1991; Hoffman, "Thermally Reversible Hydrogels Containing Biologically Active Species," in Migliaresi et al. (eds.), Polymers in Medicine III, Elsevier Science Publishers B. V., Amsterdam, 1988, pp. 161-167; Hoffman, "Applications of Thermally Reversible Polymers and Hydrogels in Therapeutics and Diagnostics," in Third International Symposium on Recent Advances in Drug Delivery Systems, Salt Lake City, Utah, Feb. 24-27, 1987, pp. 297-305; Gutowska et al., J. Controlled Release 22:95-104, 1992; Palasis and Gehrke, J. Controlled Release 18:1-12, 1992; Paavola et al., Pharm. Res. 12(12):1997-2002, 1995).

Representative examples of thermogelling polymers, and their gelatin temperature (LCST (.degree. C. )) include homopolymers such as poly(N-methyl-N-n-propylacrylamide), 19.8; poly(N-n-propylacrylamide), 21.5; poly(N-methyl-N-isopropylacrylamide), 22.3; poly(N-n-propylmethacrylamide), 28.0; poly(N-isopropylacrylamide), 30.9; poly (N, n-diethylacrylamide), 32.0; poly(N-isopropylmethacrylamide), 44.0; poly(N-cyclopropylacrylamide), 45.5; poly(N-ethylmethyacrylamide), 50.0; poly(N-methyl-N-ethylacrylamide), 56.0; poly(N-cyclopropylmethacrylamide), 59.0; poly(N-ethylacrylamide), 72.0. Moreover thermogelling polymers may be made by preparing copolymers between (among) monomers of the above, or by combining such homopolymers with other water soluble polymers such as acrylmonomers (e.g., acrylic acid and derivatives thereof such as methylacrylic acid, acrylate and derivatives thereof such as butyl methacrylate, acrylamide, and N-n-butyl acrylamide). Other representative examples of thermogelling polymers include cellulose ether derivatives such as hydroxypropyl cellulose, 41.degree. C.; methyl cellulose, 55.degree. C.; hydroxypropylmethyl cellulose, 66.degree. C.; and ethylhydroxyethyl cellulose, and Pluronics such as F-127, 10-15.degree. C.; L-122, 19.degree. C.; L-92, 26.degree. C.; L-81, 20.degree. C.; and L-61, 24.degree. C.

A wide variety of forms may be fashioned by the polymeric carriers of the present invention, including for example, rod-shaped devices, pellets, slabs, or capsules (see e.g., Goodell et al., Am. J. Hosp. Pharm. 43:1454-1461, 1986; Langer et al., "Controlled release of macromolecules from polymers", in Biomedical Polymers, Polymeric Materials and Pharmaceuticals for Biomedical Use, Goldberg, E. P., Nakagim, A. (eds.) Academic Press, pp. 113-137, 1980; Rhine et al., J. Pharm. Sci. 69:265-270, 1980; Brown et al., J. Pharm. Sci. 72:1181-1185, 1983; and Bawa et al., J. Controlled Release 1:259-267, 1985).

Therapeutic agents may be linked by occlusion in the matrices of the polymer, bound by covalent linkages, or encapsulated in microcapsules. Within certain preferred embodiments of the invention, therapeutic compositions are provided in non-capsular formulations such as microspheres (ranging from nanometers to micrometers in size), pastes, threads of various size, films and sprays.

Another aspect of the present invention is to provide a therapeutic composition and animal feed. The therapeutic composition of the present invention can be encapsulated using a polymeric carrier as described above and then added to a feed by any known means of applying it to feed such as for example, by mechanical mixing, spraying, etc. The therapeutic composition includes, for example, an amount of at least one bacteriocin and/or antagonistic bacteria effective to at least reduce the levels of colonization by at least one target bacteria in an animal, such as for example approximately 0.5 grams each of a lactocin and/or enterocin/1000 grams, approximately 1.25 grams of a polymeric carrier such as polyvinylpyrrolidone/1000 grams, and about 8.6% of a diluent such as water/1000 grams mixed with any granular component that is digestable, such as for example, milled maize grain; ground grains such as for example oats, wheat, buckwheat; ground fruits such as for example, pears, etc. The therapeutic composition is then added to any type of animal feed in amounts effective to at least reduce the levels of colonization of at least one target bacteria such as for example in ratios of bacteriocin to feed of about 1:10 to about 1:100. For purposes of the present invention, examples of animal feed include green fodder, silages, dried green fodder, roots, tubers, fleshy fruits, grains, seeds, brewer's grains, pomace, brewer's yeast, distillation residues, milling byproducts, byproducts of the production of sugar, starch or oil production, and various food wastes. The product can be added to the animal feedstuffs for cattle, poultry, rabbit, pig, or sheep rearing, etc. It can be used mixed with other feed additives for these stock.

The following examples are intended only to further illustrate the invention and are not intended to limit the scope of the invention as defined by the claims.

EXAMPLE 1

Two novel antagonistic strains, *Lactobacillus salivarius* designated NRRL B-30514 (Strain PVD32) and *Lactobacillus acidophilus*, designated NRRL B-30510 (Strain LWP320), producing bacteriocins were isolated from the ceca and crop of broilers. The ceca and crop were preliminarily emptied and washed twice with approximately 100 ml of sterile 0.85% w/v saline solution (normal saline). The ceca and crop material was suspended in sterile saline solution, pH about 7.0. About 0.1 ml of a 10-fold diluted suspension was plated directly onto selective MRS agar. Plates were anaerobically incubated at about 37° C. for about 16-18 hours. At least 10 colonies specific for *Lactobacillus* spp. were selected from each sample. *Lactobacilli* were identified using the APO 50 CHL microtest system (bioMerieux, France).

Strains *Lactobacillus salivarius* PVD 32 and *Lactobacillus acidophilus* LWP320 were grown at approximately 37° C. for about 24 hours on MRS Agar. The two strains are facultative anaerobes, Gram-positive nonmotile rods capable of growth at about 30°, 37°, and 42° C. Strain PVD 32 grows on MRS agar producing circular to regular-shaped, smooth, convex colonies with sharp margins that are about 1-3 mm in diameter after microaerophilic incubation for about 18-24 hours at about 37° C. Strain LWP320 grows on MRS agar producing albescent, semiopaque colonies that are about 0.5 to about 0.8 mm in diameter after microaerophilic incubation for about 24 hours at 37° C.

*Enterococcus faecalis* LWP21 and *Enterococcus durans* LWP26 were grown at about 37° C. for about 24 hours on MRS agar. They are Gram-positive, facultative anaerobes, nonmotile cocci capable of growth at about 30°, 37°, and 42° C. Strain LWP21 grows on MRS agar producing albescent semiopaque colonies that are opaque after microaerophilic incubation for about 24 hours. After about 48 hours microaerophilic incubation at about 37° C., the colonies are about 0.8 to about 1.0 mm in diameter.

The results in the API 50CHL and EN-COCCUS galleries using API 50 CHL suspension medium, are presented below in Table 1. Results shown below in Table 2 indicate that strain PVD32 is *Lactobacillus salivarius*, strain LWP320 is *Lactobacillus acidophilus*, strain LWP21 as *Enterococcus faecalis*, and strain LWP26 as *Enterococcus durans*.

Target bacteria for assessing antagonistic activity of antagonistic isolates included strains of L4 and B1 of *C. jejuni* isolated from broilers in Russia and *Campylobacter jejuni* ATCC 11168, several species from the family Enterobacteriaceae, *Pseudomonas aeruginosa* strain ATCC 9027, *Staphylococcus aureus*, and *Listeria monocytongenes*, were used as test cultures to evaluate isolates for antagonistic activity. Cultures of *C. jejuni* were grown either on brucella agar or *Campylobacter* agar supplemented with about 0.02% sodium bisulfite, about 0.05% ferrous sulfate, and about 5% partially lysed sheep blood at about 37° C. for approximately 18-24 hours under microaerobic conditions of about 5% $O_2$, about 10% $CO_2$, and about 85% $N_2$. The other strains were cultured on nutrient agar at about 37° C. or about 28° C. for *Y. enterocolitica* and *Y. pseudotuberculosis* for about 18-24 hours under aerobic conditions. Antagonistic activity of the isolates against *Campylobacter* was evaluated. Approximately 0.2 ml of the suspensions in normal saline was plated onto MRS agar and incubated at about 37° C. for about 24 hours. Agar cubes of about 0.5 $cm^3$ were cut out and transferred onto brucella agar or *Campylobacter* agar supplemented with about 5%-10% partially lysed sheep blood, about 10 micrograms/ml rifampicin, and about 2.5 u/ml of polymyxin and inoculated with approximately $10^7$ cells of *Campylobacter jejuni* per plate. Plates were incubated at about 42° C. for approximately 24 hours under microaerobic conditions as described above. Antagonistic activity was evaluated by measuring the size of the diameter of the zones of *C. jejuni* inhibition.

Antagonistic activity to *Campylobacter jejuni* was evaluated using 11,790 isolates. Out of these, 279 isolates exhibited antagonism to *C. jejuni*.

TABLE 1

Identification results in the API 50CHL and EN-COCCUS-test.

| Strains | Test (Score) | Species |
| --- | --- | --- |
| PVD32 | API 50CHL (99.9%) | *Lactobacillus salivarius* |
| LWP320 | API 50CHL (96.6%) | *Lactobacillus acidophilus* |
| LWP21 | EN-COCCUS-test (96%) | *Enterococcus faecalis* |
| LWP26 | EN-COCCUS-test (98%) | *Enterococcus durans* |

TABLE 2a

Characterization of *Lactobacillus* Strains (results in the API 50CHL).

| CARBOHYDRATES | Isolates and its properties | |
| --- | --- | --- |
| | PVD32 | LWP320 |
| 0-control | − | − |
| Glycerol | − | − |
| Erythriol | − | − |

TABLE 2a-continued

| | | |
| --- | --- | --- |
| D-Arabinose | − | − |
| L-Arabinose | − | − |
| Ribose | − | − |
| D-Xylose | − | − |
| L-Xylose | − | − |
| Adonitol | − | − |
| β-Methyl-xyloside | − | − |
| Galactose | + | + |
| D-Glucose | + | + |
| D-Fructose | + | + |
| D-Mannose | + | − |
| L-Sorbose | − | − |
| Rhamnose | + | − |
| Dulcitol | − | − |
| Inositol | − | − |
| Mannitol | + | − |
| Sorbitol | + | − |
| α-methyl D-mannoside | − | ? |
| α-methyl D-glucoside | − | ? |
| N-acetyl glucosamine | + | + |
| Amigdaline | − | + |
| Arbutine | − | ? |
| Esculine | − | − |
| Salicine | − | + |
| Cellobiose | − | + |
| Maltose | + | + |
| Lactose | + | + |
| Melibiose | + | − |
| Saccharose | + | + |
| Trehalose | + | − |
| Inuline | − | − |
| Melezitose | − | − |
| D-Raffinose | + | ? |
| Amidon | − | − |
| Glycogen | − | − |
| Xylitol | − | − |
| Gentiobiose | − | − |
| D-Turanose | − | − |
| D-Lyxose | − | − |
| D-Tagatose | − | − |
| D-Fucose | − | − |
| L-Fucose | ? | − |
| D-Arabitol | ? | − |
| L-Arabitol | − | − |
| Gluconate | − | − |
| 2 ceto gluconane | − | − |
| 5 ceto gluconane | − | − |
| Identification as | *Lactobacillus salivarius* | *Lactobacillus acidophilus* |

Characterization of *Entercoccus* Strains using the EN-COCCUS-test.

| | Isolates and its properties | |
| --- | --- | --- |
| TEST | LWP21 | LWP26 |
| L-Arabinose | − | − |
| Ribose | + | + |
| L-Sorbose | − | − |
| Mannitol | + | − |
| Sorbitol | + | − |
| Lactose | + | + |
| Melibiose | − | d |
| Saccharose | + | − |
| Melezitose | (+) | − |
| D-Raffinose | − | − |
| Arginin | + | + |
| Identification as | *Enterococcus faecalis* | *Enterococcus durans* |

TABLE 3

Inhibitory activity of isolates against test strains of *Campylobacter jejuni.*

| Antagonistic Identification | Source of Strain | Diameter (mm) of growth Inhibition of C. jejuni | | | | | |
|---|---|---|---|---|---|---|---|
| | | 11168 | B1 | L4 | F2 | KI | UW3 |
| LWP21 | broiler ceca | 7 | 5 | 4 | 5 | 2 | 4 |
| LWP26 | broiler ceca | 2 | 5 | 4 | 6 | 3 | 7 |
| LWP320 | broiler ceca | 4 | 5 | 4 | 5 | 3 | 6 |
| PVD32 | broiler crop | 5 | 5 | 4 | 5 | 4 | 6 |

EXAMPLE 2

Two novel antagonistic strains, *Enterococcus faecalis* 21 (NRRL B-30645), and *Enterococcus durans* 26 (NRRL B-30511), producing bacteriocins, were isolated from cecal and crop smears of healthy broilers. Ceca and crops were emptied and washed twice with sterile 0.085% w/v saline solution (Normal saline) at about pH 7.0. The ceca and crop material were suspended in sterile normal saline at about pH 7.0. About 0.1 ml of a 10-fold diluted suspension was plated directly onto MRS selective medium and plates were incubated at about 37° C. for about 24-48 hours. *Enterococci* were identified using the microtest kit EN-COCCUS.

*Campylobacter jejuni* ATCC 11168 was used as a test culture to evaluated isolates for antagonistic activity as described above in Example 1. Thirty-three other strains were used as test cultures to evalutate isolate antagonistic activity as described above in Example 1. Antagonistic activity of the isolates against *Campylobacter* was also evaluated as described above in Example 1.

Antagonistic activity to *Campylobacter jejuni* was evaluated using 1,200 isolates derived from about 125 broilers. Out of these, 63 isolates exhibited antagonism to *C. jejuni* ATCC 11168. The ability to produce bacteriocins during cultivation in MRS broth was studied for the 12 most active isolates (See Tables 1-3 above).

EXAMPLE 3

Crude antimicrobial preparations were prepared by ammonium sulfate precipitation only from cultures of antagonistic strains of *Lactobacillus* grown on starvation medium:

| | |
|---|---|
| $K_2HPO_4$ | 6.0 grams |
| $KH_2PO_4$ | 0.2 gram |
| $(NH_4)_2SO_4$ | 0.2 gram |
| $MgSO_4$ | 0.1 gram |
| glucose | 9.0 grams |
| histidine | 0.08 gram |
| arginine | 0.02 gram |

Add distilled $H_2O$ to 1,000 ml, pH 7.2 for about 18 hours under aerobic conditions at about 37° C. The culture fluids were centrifuged at about 12,000×g, for about 10 minutes. The resulting supernatants were adjusted to pH of about 6.2 by adding 1N NaOH and about 130 U/ml catalase was added to remove organic acids, hydrogen peroxide, and inhibiting factors. Antagonistic peptides were isolated from the supernatant by a combination of ammonium sulfate precipitation, desalting chromatography, and gel filtration to produce a crude preparation (CAP). CAP samples were filtered through 0.22μ filters (Millipore, Bedford, Mass.).

EXAMPLE 4

Isolates of *Enterococcus* exhibiting antimicrobial activity from Example 2 above, were cultured in MRS broth (HiMedia;)

| | |
|---|---|
| MRS broth | 15 grams |
| Lactose | 0.05 gram |

Add distilled $H_2O$ to about 1000 ml, pH approximately 7.2 at about 37° C. for about 18 hours under aerobic conditions. Culture fluids were harvested and centrifuged at about 12,000×g for about 10 minutes. The resulting supernatants were adjusted to pH of about 6.2 by adding 1N NaOH and about 130 U/ml catalase was added to remove organic acids, hydrogen peroxide, and inhibiting factors. Antagonistic peptides were isolated from the supernatant by a combination of ammonium sulfate precipitation, desalting chromatography, and gel filtration to produce a crude antimicrobial preparation (CAP). CAP samples were filtered through 0.22μ filters (Millipore).

EXAMPLE 5

The spectrum of antimicrobial activity of the CAPs was determined using a spot test. Approximately 1 ml of a sterile crude antimicrobial preparation (CAP), obtained as in Examples 3 and 4 above, were diluted with approximately 1 ml of phosphate-sodium buffer (pH about 7.0) and sterilized as above in Examples 3 and 4. Approximately 10 microliters of each sample were plated onto blood-supplemented *Campylobacter* agar or Nutrient agar previously seeded with cells of target bacteria. Plates containing cultures of *C. jejuni* were grown at about 42° C. under microaerobic conditions, *Y. enterocolitica* and *Y. pseudotuberculosis* were cultured aerobically at about 28° C., and other bacterial strains were incubated aerobically at about 37° C. for about 24 or 48 hours. Identification was based on inhibition areas produced by the target bacteria. Activity of CAP was expressed in arbitrary units (AU) per one milliliter of the preparation at which a visible zone of inhibition of the growth of culture appears (Henderson et al., Archives of Biochemistry and Biophysics, Volume 295, 5-12, 1992; herein incorporated by reference). All experiments were conducted in duplicate.

Tables 4 and 5 below show the antagonistic activity of the crude antimicrobial preparations prepared for *Lactobacillus* in Example 3, and *Enterococcus* in Example 4.

Two isolates of *Lactobacillus* species inhibited the growth of *Campylobacter jejuni* (Table 3). The isolates were identified using the API 50CHL test (bioMerieux, France) and are *Lactobacillus salivarius* -PVD32 (NRRL B-30514) and *Lactobacillus acidophilus* LWP320 (NRRL B-30510). As seen in Table 4, all these strains produce lactocin with a wide spectrum of antibacterial activity. They inhibit growth of both Gram-positive and Gram-negative microorganisms. Lactocin OR-7 is most active against *C. jejuni*.

Two isolates of *Enterococcus* species inhibited the growth of *C. jejuni* (Table 3). The isolates were identified using the ENCOCCUS-test as *Enterococcus faecalis* (isolate LWP21)

(NRRL B-30645) and *Enterococcus durans* (isolate LWP26) (NRRL B-30511). Both strains produce enterocins with a wide spectrum of activity suppressing both Gram-positive and Gram-negative microorganisms. Enterocin 21 produced by *E. faecalis* is unique in that it inhibits the growth of all 33 test strains including *Proteus vulgaris* and *Morganella morganii* which are especially resistant to bacteriocins of different origins.

TABLE 4

Activity of lactocin and lactococcin produced by *Lactobacillus* spp. and *Lactococcus* spp. in spot test (AU/ml).

| Test Strains | OR-7 Lactcin | LWP320 Latocin |
|---|---|---|
| *C. jejuni* ATTC 11168 | 3200 | 1600 |
| *C. jejuni* L4 | 3200 | 1600 |
| *C. jejuni* UV3 | 3200 | 800 |
| *C. jejuni* F2 | 3200 | 800 |
| *S. enteritidis* 1 | 1600 | 800 |
| *S. enteritidis* 4 | 1600 | 800 |
| *S. enteritidis* 204 | 800 | 800 |
| *S. enteritidis* 237 | 1600 | 800 |
| *S. gallinarum pullorum* | 800 | 400 |
| *S. typhimurium* 320 | 1600 | 400 |
| *S. typhimurium* 383/60 | 1600 | 800 |
| *S. choleraesuis* 370 | 1600 | 800 |
| *S. choleraesuis* 434/4 | 800 | 400 |
| *E. coli* O157:7 EDL 933 | 1600 | 1600 |
| *E. coli* O157:7 904 | 3200 | 3200 |
| *E. coli* O157:7 J61 | 3200 | 400 |
| *E. coli* O157:7 131 | 3200 | 800 |
| *Citrobacter freundii* | 1600 | 400 |
| *Klebsiella pneumoniae* | 1600 | 200 |
| *Sh. Dysenteriae* | 1600 | 200 |
| *Y. enterocolitica* 03 | 1600 | 400 |
| *Y. enterocolitica* 09 | 1600 | 200 |
| *Y. enterocolitica* 11 | 800 | 400 |
| *Y. pseudotuberculosis* ser 4 | 1600 | 200 |
| *Y. pseudotuberculosis* ser 14 | 1600 | 200 |

TABLE 5

Activity of enterocins produced from *Enterococcus faecalis* 21 and *Enterococcus durans* 26.

| Test Strain | *E. faecalis* CAP | *E. faecalis* Peak I | *E. faecalis* Peak II | *E. faecalis* Peaks I & II | *E. durans* CAP |
|---|---|---|---|---|---|
| *C. jejuni* ATCC 11168 | 12800 | — | 400 | 12800 | 6400 |
| *C. jejuni* L4 | 6400 | — | 400 | 6400 | 3200 |
| *C. jejuni* UV3 | 6400 | — | 400 | 6400 | 3200 |
| *C. jejuni* F2 | 6400 | — | 400 | 6400 | 3200 |
| *S. enteritidis* 1 | 1600 | — | 400 | 1600 | 3200 |
| *S. enteritidis* 4 | 1600 | — | 400 | 1600 | 3200 |
| *S. enteritidis* 204 | 1600 | — | 400 | 1600 | 3200 |
| *S. enteritidis* 237 | 1600 | — | 400 | 1600 | 3200 |
| *S. gallinarum pullorum* | 3200 | — | 800 | 3200 | 1600 |
| *S. typhimurium* 320 | 3200 | — | 800 | 3200 | 1600 |
| *S. typhimurium* 386/60 | 3200 | — | 800 | 3200 | 3200 |
| *S. choleraesuis* 370 | 3200 | — | 400 | 3200 | 3200 |
| *S. cholerasuis* 434/4 | 1600 | — | 400 | 1600 | 3200 |
| *E. coli* O157:7 EDL933 | 3200 | — | 400 | 3200 | 1600 |
| *E. coli* O157:7 904 | 3200 | — | 800 | 3200 | 1600 |
| *E. coli* O157:7 J61 | 3200 | — | 400 | 3200 | 3200 |
| *E. coli* O157:7 131 | 3200 | — | 200 | 3200 | 3200 |
| *Citrobacter freundi* | 6400 | — | 400 | 6400 | 1600 |
| *Klebsiella pneumoniae* | 1600 | — | 200 | 1600 | 1600 |

TABLE 5-continued

Activity of enterocins produced from *Enterococcus faecalis* 21 and *Enterococcus durans* 26.

| Test Strain | E. faecalis CAP | E. faecalis Peak 1 | E. faecalis Peak II | E. faecalis Peaks I & II | E. durans CAP |
|---|---|---|---|---|---|
| *Sh. dysenteriae* | 6400 | — | 800 | 6400 | 1600 |
| *Y. enterocolitica* 03 | 6400 | — | 400 | 6400 | 3200 |
| *Y. enterocolitica* 09 | 3200 | — | 400 | 3200 | 3200 |
| *Y. enterocolitica* 11 | 3200 | — | 400 | 3200 | 1600 |
| *Y. pseudotuberculosis* ser 4 | 3200 | — | 400 | 3200 | 1600 |
| *Y. pseudotuberculosis* 14 | 3200 | — | 400 | 3200 | 1600 |
| *Proteus mirabilis* | 800 | — | 200 | 800 | — |
| *Morganella morganii* | 800 | — | 200 | 800 | — |
| *Pseudomonas aeruginosa* ATCC 9027 | 6400 | — | 400 | 6400 | — |
| *L. monocytogenes* 9-72 | 6400 | — | 800 | 6400 | 3200 |
| *L. monocytogenes* 9-30 | 12800 | — | 800 | 12800 | — |
| *L. monocytogenes* A | 6400 | — | 800 | 6400 | 3200 |
| *Staphylococcus aureus* | 6400 | — | 800 | 6400 | 1600 |
| *Staphylococcus epidermidis* 4 | 3200 | — | 400 | 3200 | 1600 |

EXAMPLE 6

CAPs and bacteriocins were electrophoresed by SDS-PAGE using about 15% agarose gel weight and about 1% SDS (9×12 cm) in Tri-glycine buffer. After electrophoresis at about 100 mA for approximately 4 hours, gels were fixed with a solution containing approximately 15% ethanol and approximately 1% acetic acid. The gels were then washed with distilled water for approximately 4 hours. To determine molecular weights of protein fractions, the gel was stained with a solution containing approximately 0.15% Coomassi Brilliant Blue R-250 (Sigma, USA) about 40% ethanol, and about 7% acetic acid. Gels were washed sequentially with phosphate buffered saline (PBS) for about 1.5 hours and deionized water for about 3 hours. Washed gels were tested against three target bacteria, *C. jejuni* ATCC 11168, *E. coli* 0157:H7 904, and *S. enteritidis* 237 by the method of Bhunia et al. (Journal of Industrial Microbiology, Volume 2, 319-322, 1987; herein incorporated by reference). The gels were placed in Petri dishes, covered with about 5% lysed sheep blood-semi-solid *Campylobacter* agar (about 0.75%) or semi-solid agar (0.7%), and seeded with cells of the test strains. Plates containing *C. jejuni* were incubated at about 42° C. for approximately 48 hours under microaerobic conditions, *E.coli* 0157:H7 and *S. enteritidis* at about 37° C. for approximately 24 hours. Assessment was based on visualization of zones of the inhibited growth of the test strains in the presence of bacteriocins. Activity of the purified bacteriocins was evaluated (Table 6 for *Lactobacillus* species and Table 7 for *Enterococcus* species).

Specimens of CAPs and bacteriocins were placed on IEF gels (pH approximately 3.1-10.0) (Novex, San Diego, Calif.). The gels were run at about 100V for about 1 hour, 200V for about 2 hour, and 500V for about 30 minutes in XCM II™ Mini-Cell (Novex). Gels were washed with distilled water for about 30 seconds without fixation followed by staining with Coomassie Brilliant Blue R-250 (Sigma, USA) to determine isoelectric points (pI) of the bacteriocins and their ability to inhibit the growth of the test strains as presented below in Tables 6 for lactocins and Table 7 for enterocins.

As seen in FIG. 1, the CAP OR7 of *L. salivarius* PVD 32 contains three protein fractions of about 6 kDa, about 16 kDa, and about 40 kDa. To measure their activity, stained electrophoretic strips comprising the peptides were placed onto semisolid *Campylobacter* agar inoculated with cells of *C. jejuni* ATCC 11168, *S. enteritidis*, and *E. coli* 0157:H7. The about 6 kDa fraction was found to be active against all three test strains. Isoelectrofocusing identified a fraction of pI=about 9.0 which showed activity against all three test strains.

Figure 2:
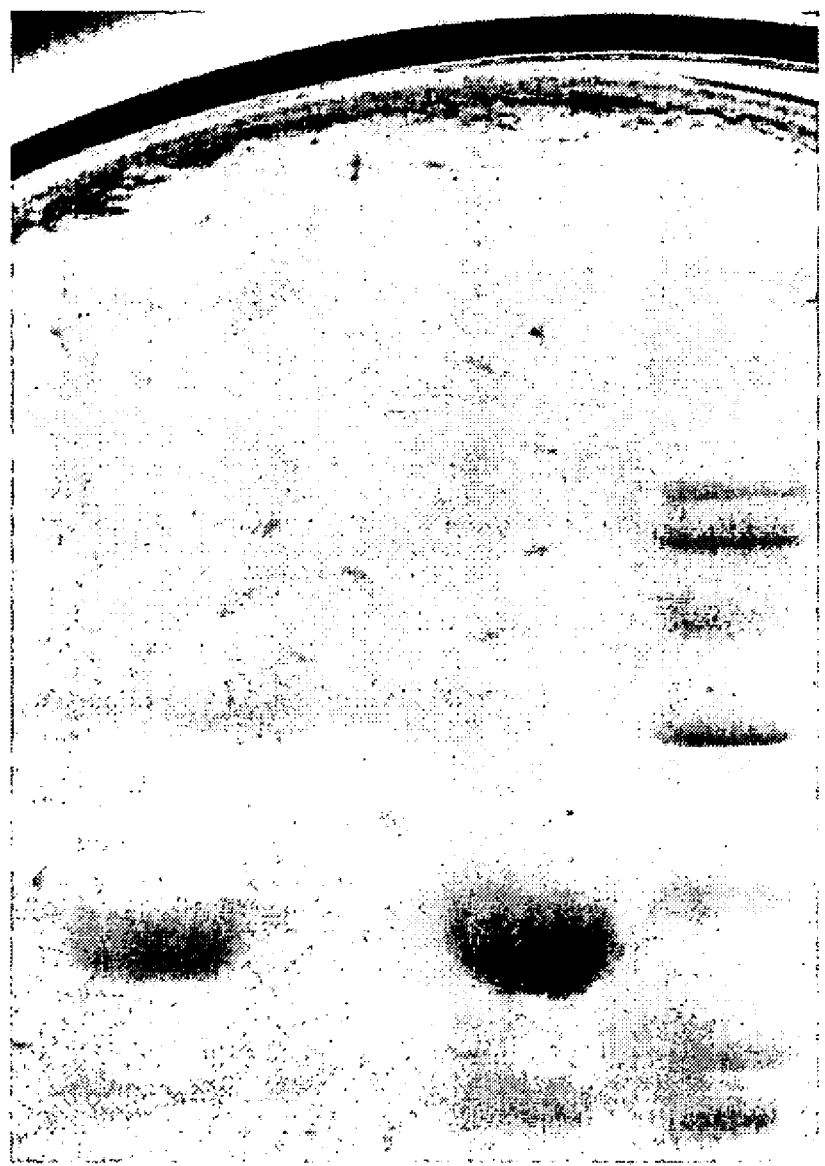
FIG. 2 is a photograph showing direct detection of bacteriocin LWP320 and LWP26 after SDS-PAGE. The gel was overlaid with *Campylobacter jejuni* to determine which band(s) corresponds to the antimicrobial activity and the molecular weight associated with the activity. Lane 3—Molecular Weight Markers LMW Range 3,000-43,000(AMERSHAM PHARMACIA BIOTECH): 3,000, 11,400, 18,000, 21,000, and 43,000 Da. The band in lane 1—bacteriocin LWP320, the band in Lane 2—Bacteriocin LWP26, which corresponds to the antimcrobial activity, the zone of growth inhibition, had a mass of about 6,000 and about 3,000 Da, respectively. Other bands did not show antimicrobial activity.

As seen in FIG. 2, the pure lactocin LWP320 of *L. acidophilus* LWP320 and the pure enterocin LWP26 of *E. durans* LWP26 contains protein fractions of about 6 kDa and about 3 kDa, respectively. To measure their activity, stained electrophoretic strips comprising the peptides were placed onto semisolid *Campylobacter* agar inoculated with cells of *C. jejuni* ATCC 11168, *S. enteritidis*, and *E. coli* 0157:H7. The about 6 kDa and about 3 kDa fractions were found to be active against all three test strains. Isoelectrofocusing identified fractions of pI=about 8.5 and about 7.8 respectively, which showed activity against all three test strains.

Figure 3:
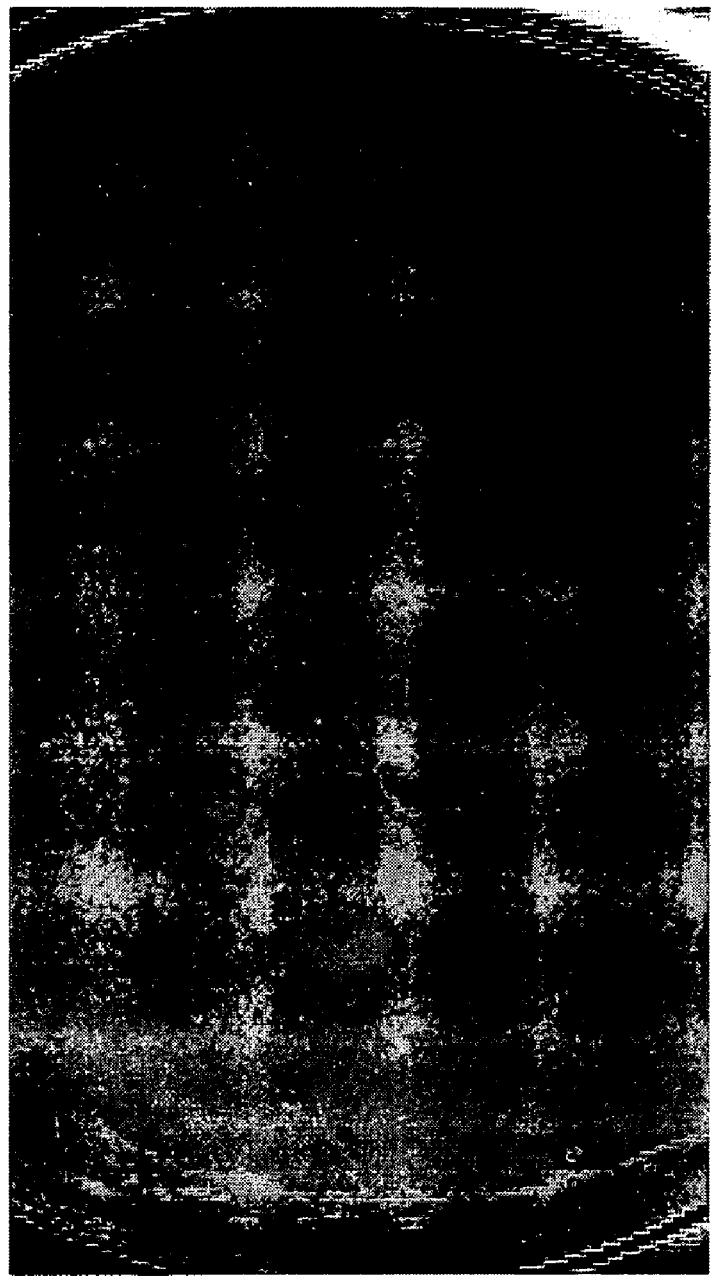
FIG. 3 is a photograph showing the direct detection of enterocin LWP21 after SDS-PAGE. The gel was overlaid with *Campylobacter jejuni* to determine which band(s) corresponds to the antimicrobial activity and molecular weight of the active band. Lane 4—Molecular Weight Markers LMW Range 1060-43,000 (AMERSHAM PHARMACIA BIOTECH): 1,060, 2,500, 3,500, 14,400, 20,000, 30,000, and 43,000 Da. The band in lane 1 (enterocin LWP21 after SP-Sepharose), and the band in lane 2 (peak 2 after phenyl-Sepharose CL-4B) which corresponds to the antimicrobial activity, the zone of growth inhibition (see arrow), had a mass of about 6,000 Da. The band in lane 3 (peak after phenyl-Sepharose CL-4B), had a mass of about 3,000 Da. Other bands did not show antimicrobial activity.

As seen in FIG. 3, the isolated enterocin LWP21 of *E. faecalis* LWP21 comprises two protein fractions of about 3.0 kDa (peak 1) and about 6.0 kDa (peak 2). To determine antimicrobial activity, the electrophoretic bands were placed onto semi-solid *Campylobacter* agar inoculated with *C. jejuni* ATTC 11168, *S. enteritidis*, and *E. coli* 0157:H7. The about 6.0 kDa fraction was active against all three strains. No antibacterial activity was observed for the about 3.0 kDa fraction. For the isolated enterocin LWP26, isoelectrofocusing identified a single protein fraction of pI of about 7.8 which was antagonistic to all three tested strains (Table 7). The highest activity was associated with enterocin LWP21 peak 1+peak 2 fractions in the spot-test while the lowest activity was shown with the SDS-PAGE and IEF

TABLE 6

Antimicrobial activity of CAPs of lactocins determined by spot-test, SDS-PAGE, and IEF.

| CAP | Test Strain | Inhibiting activity in Spot Test (AU/ml) | Inhibiting activity in SDS-PAGE (kDa) | Inhibiting activity in IEF (pI) |
|---|---|---|---|---|
| OR-7 lactociin | *C. jejuni* ATCC 11168 | 3200 | M.W. = 6.0 | 9.0 |
| | *S. enteritidis* 204 | 800 | M.W. = 6.0 | 9.0 |
| | *E. coli* O157:H7 904 | 3200 | M.W. = 6.0 | 9.0 |
| LWP320 lactocin | *C. jejuni* ATCC 11168 | 1600 | M.W. = 6.2 | 8.5 |
| | *S. enteritidis* 204 | 800 | M.W. = 6.2 | 8.5 |
| | *E. coli* O157:H7 904 | 800 | M.W. = 6.2 | 8.5 | et al., (Journal of Biological Chemistry, Volume 193, 1951). The fractions inhibiting the growth of *C. jejuni* were further purified by cation exchange chromatography using a CM-Sepharose column (Pharmacia, 2.5×20 cm). The CM-Sepharose column was equilibrated with buffer C (50 mM citrate-phosphate buffer pH about 5.0) at a flow rate of about 8 ml/min. Bacteriocins were eluted with about 8 mM of buffer C in the presence of NaCl at concentrations of from about 0.1% to about 0.8% at a flow rate of about 8 ml/min. Antimicrobial activity and protein concentrations for each fraction were determined. The purified fractions were designated lactocins OR7 and LWP320.

The purified OR7 and LWP320 were evaluated using SDS-PAGE and isoelectrofocusing as described above in example 4. The most active fraction (OR7) was a peptide with a molecular weight of about 6 kDa and a pI of about 9.0 (FIG. 1 and Table 6) and active fraction LWP320 was a peptide with a molecular weight of about 6 kDa, pI of about 8.5 (FIG. 3 and Table 6).

*Enterococcus* bacteriocins from CAPs were purified using a two-step procedure: ion exchange chromatography and hydrophobic chromatography. Active CAP fractions obtained

TABLE 7

Characterization of active fractions of enterocins LWP21 and LWP26 based on results from SDS-PAGE and Isoelectrofocusing.

| Enterocins | Test Strains | Activity in Spot Test (AU/ml) | Molecular Weights based on SDS-PAGE (kDa) | Isoelectric Points of bacteriocins |
|---|---|---|---|---|
| Enterocin LWP21 Peak I fraction | *C. jejuni* ATCC 11168 | — | 3.0 | 5.6 |
| | *S. enteritidis* 204 | — | 3.0 | 5.6 |
| | *E. coli* O157:H7 904 | — | 3.0 | 5.6 |
| Enterocin LWP21 Peak II fraction | *C. jejuni* ATCC 11168 | 400 | 6.1 | 8.4 |
| | *S. enteritidis* 204 | 400 | 6.1 | 8.4 |
| | *E. coli* O157:H7 904 | 400 | 6.1 | 8.4 |
| Enterocin LWP21 Peak I + Peak II fraction | *C. jejuni* ATCC 11168 | 12800 | 3.0, 6.1 | 5.6, 8.4 |
| | *S. enteritidis* 204 | 1600 | 3.0, 6.1 | 5.6, 8.4 |
| | *E. coli* O157:H7 904 | 3200 | 3.0, 6.1 | 5.6, 8.4 |
| Enterocin LWP26 | *C. jejuni* ATCC 11168 | 6400 | 3.0 | 7.8 |
| | *S. enteritidis* 204 | 3200 | 3.0 | 7.8 |
| | *E. coli* O157:H7 904 | 1600 | 3.0 | 7.8 |

EXAMPLE 7

Bacteriocins obtained as a crude antimicrobial preparation, as described above in Example 2, were purified by gel filtration and ion exchange chromatography. Crude antimicrobial preparations (CAPs) of lactocin OR7 and lactocin LWP320 were injected into a Superose 12HR 16/50 column (Pharmacia, 1.6×50 cm) equilibrated with about 75 ml of phosphate-sodium buffer, pH approximately 5.9. The preparations were eluted with the same buffer at a flow rate of about 8 ml/min. Activities of the eluted fractions were tested against *Campylobacter jejuni* ATCC 11168. The concentration of the proteins was measured by using the method described by Lowry in Example 4 were injected into a SP-Sepharose Fast Flow Column (V-30 ml) equilibrated with buffer C (20 mM phosphate-sodium, pH about 7.8) at a flow rate of about 18 ml/minute. The column was washed with four volumes of buffer C and fractions were eluted with about 100 ml of 0.5 M NaCl in buffer C. Fraction activity was determined using the spot test as described above in Example 5 using *C. jejuni* ATCC 11168. The fractions capable of inhibiting the growth of *C. jejuni* were injected in a Phenyl-Sepharose CL-4B column equilibrated with buffer D (0.06 M borate buffer, pH about 8.5) containing 0.2 M NaCl. The column was washed with four volumes of buffer D. Fractions were eluted with about 4 ml of buffer D containing about 70% ethanol (vol/ vol). Antagonism of each fraction was measured using the spot test. Pure preparations were obtained by methods of cation-exchange rechromatography on SP-Sepharose, as well as on Phenyl-Sepharose CL-4B. The concentration of protein was determined using the method of Lowry (supra). The isolated fractions were designated as enterocins LWP21 and LWP26.

The isolated LWP21 and LWP26 fractions were evaluated using SDS-PAGE and isoelectrofocusing as described above in Example 4. The most active fraction 2 for LWP21 was a peptide with a molecular weight of about 6 kDa and a pI of about 8.4 (FIG. 2 and Table 7) and nonactive fraction 1 for LWP21 was a peptide with a molecular weight of about 3 kDa, PI of about 5.6 (FIG. 2 and Table 7). The most active fraction for LWP26 was a peptide with a molecular weight of about 3 kDa and a pI of about 7.8 (FIG. 3 and Table 7).

The amino acid sequences of purified bacteriocins were determined by Edman degradation using a 491 cLC automatic sequencer (Applied Biosystems, USA). The bacteriocins were hydrolyzed in about 6M HCl under a vacuum at approximately 110° C. for about 72 hours. Molecular weights were determined by mass spectrometry using a Voyager-DERP (Perkin-Elmer, USA). The MALDI-TOF system, a matrix-assisted laser desorption ionization time of flight system, was used along with matrix, 2-cyano-hydroxycinnamic acid. The amino acid sequences for the four bacteriocins are:

```
                                          SEQ ID NO 1
OR7: KTYYGTNGVHCTKNSLWGKVRLKNMKYDQNTTYMGRLQDILLGWA
TGAFGKTFH

SEQ ID NO 2
LWP320: ARKYGNGVCGSKWINNGGFQVIGNNAAANLTNWGEAFASATK
SGCSATTCIINAMA

SEQ ID NO 3
LWP21 (FRACTION 1): FNIRGGYNFGKSVRHVVDAIGNMAGIIKL

SEQ ID NO 4
LWP21 (FRACTION 2): VFHAYSARGVRNNYKCAGVPDAIGCAVRGI
FIHGYSLQWMQVKWGWLFK

SEQ ID NO 5
LWP26: TKTTRGNGVNKECWETYKAGTVDILWASWSK
```

Calculated molecular weight of the OR7 peptide was about 6,000 Da. Analysis by MALDI-TOF revealed the following molecular weight for OR7: 5,123 Da.

Calculated molecular weight of the LWP320 peptide was about 6,000 Da. Analysis by MALDI-TOF revealed the following molecular weight for LWP320: 5,858 Da.

Calculated molecular weight of the LWP21 peptide (Fraction 1) was about 3,000 Da. Analysis by MALDI-TOF revealed the following molecular weight for LWP21 (Fraction 1): 2,786 Da.

Calculated molecular weight of the LWP21 peptide (Fraction 2) was about 6,000 Da. Analysis by MALDI-TOF revealed the following molecular weight for LWP21 (Fraction 2): 4,986 Da.

Calculated molecular weight of the LWP26 peptide was about 3,000 Da. Analysis by MALDI-TOF revealed the following molecular weight for LWP26: 3,231 Da.

TABLE 8

Biochemical purification of lactocin OR7.

| Sample | Volume (ml) | Protein (mg/ml) | Specific Activity AU/mg | Purity (%) |
|---|---|---|---|---|
| Culture Supernatant | 150 | 1.2 | 13034 | 0 |
| CAP ($(NH_4)_2SO_4$ precipitation) | 9.8 | 0.9 | 19174 | 9.09 |
| Superose 12 Gel Filtration | 6 | 0.4 | 58312 | 82.3 |
| CM-Sepharose cation exchange chromatography | 1.3 | 0.14 | 532317 | 93.8 |

TABLE 9

Biochemical purification of Enterocin LWP21

| Sample | Volume (ml) | Protein (mg/ml) | Specific Activity (AU/mg) | Purity (%) |
|---|---|---|---|---|
| Culture Supernatant | 1500 | 2.3 | 17932 | 0 |
| CAP ($(NH_4)_2SO_4$ precipitation) | 4.5 | 1.2 | 24142 | 10.2 |
| SP-Superose Fast Flow | 2.1 | 0.9 | 79243 | 80.2 |
| Phenyl-Sepharose CL-4B | 1.3 | 0.4 | 238732 | 93.3 |

EXAMPLE 8

The influence of enzymes, temperature, and pH on bacteriocin activity was determined. About 10 μl of one of the following enzymes were transferred into tubes containing about 20 ml of bacteriocins: beta-chymotrypsin-about 100 mg/ml, proteinase K-about 200 mg/ml, papain-about 60 mg/ml, lysozyme-about 75 mg/ml, and lipase-about 100 mg/ml (all from Sigma-Aldrich Corp., St. Louis Mo.). After about a three hour incubation period at about 37° C., the mixture of bacteriocin and enzyme was analyzed for antimicrobial activity using the spot test as in Example 5. Untreated bacteriocins served as positive controls.

To study the thermostability of bacteriocins, about a 2 mg/ml sample was boiled in a water bath for about 15 minutes, cooled, and assessed in terms of their antimicrobial activity using the spot test. Approximately 2 mg/ml of bacteriocin was used to evaluate the effect of pH. About 2 milliliters of sterile solutions, about 10 mM NaOH or about 10 mM HCl was added to samples to test pH from about 3 to about 10. Samples were incubated at about 37° C. for about 2 hours and 24 hours, and at about 90° C. for about 20 minutes. Samples were adjusted to pH about 7.2 by addition of about 4 mM sterile phosphate buffer and analyzed for their antimicrobial activity using the spot test as described above in Example 5.

The bacteriocins lost their antimicrobial activity after being treated with beta-chymotrypsin, proteinase K, and papain, but retained it when treated with lysozyme, lipase, or heating to about 90° C. (Tables 10 and 11). They were stable at different values of pH ranging from about 3.0 to about 9.0, but became inactive at about pH 10 (Tables 12 and 13). Enterocins lost their activity at pH about 9.1 and about 10.

TABLE 10

Effect of Enzymes and Temperature on antimicrobial activity of OR7.

| Treatment | Activity* |
|---|---|
| beta-chymotrypsin | – |
| proteinase K | – |
| papain | – |
| chymotrypsin | |
| lipase | |
| 90° C., 15 minutes | |

*activity against *C. jejuni* ATCC 11168 in spot test
(+) presence of activity
– loss of activity after treatment

TABLE 11

Effect of Enzymes and Temperature on antimicrobial activity of Enterocin LWP21 and Enterocin LWP26.

| Treatment | Activity* |
|---|---|
| beta-chymotrypsin | – |
| proteinase K | – |
| papain | – |
| lysozyme | + |
| lipase | + |
| 90° C., 15 minutes | + |

*activity against *C. jejuni* ATCC 11168 in spot test.
+ presence of activity after treatment
– loss of activity after treatment

TABLE 12

Effect of pH on activity of lactocin OR7.

| pH | Activity* in 2 hours at 37° C. | Activity* in 24 hours at 37° C. | Activity in 20 minutes at 90° C. |
|---|---|---|---|
| 3.0 | + | – | + |
| 5.0 | + | + | + |
| 6.2 | + | + | + |
| 7.0 | + | + | + |
| 8.4 | + | + | + |
| 9.1 | + | – | – |
| 10.0 | – | – | – |

*activity against *C. jejuni* ATCC 11168 in spot test
+ presence of activity after treatment
+ loss of activity after treatment

TABLE 13

Effect of pH on activity of enterocin LWP21 and LWP26.

| pH | Activity* 2 hours at 37° C. | Activity* 24 hours at 37° C. | Activity* 20 minutes at 90° C. |
|---|---|---|---|
| 3.0 | – | – | – |
| 5.0 | + | + | + |
| 6.2 | + | + | + |
| 7.0 | + | + | + |
| 8.4 | + | + | + |
| 9.1 | – | – | – |
| 10.0 | – | – | – |

*activity against *C. jejuni* ATCC 11168 in spot test
+ presence of activity after treatment
– loss of activity after treatment

EXAMPLE 9

Bacteriocin OR7 was purified as described in Example 5. Purified bacteriocin OR7 was added at a concentration of approximately 250 mg per kilogram of commercial poultry feed in polyvinylpyrrolidone as is known in the art. About 100 grams of a therapeutic composition made up with milled maize grain contains approximately 0.5 grams bacteriocin OR7, approximately 1.25 grams of polyvinylpyrrolidone, and approximately 8.6% water. About 100 grams of this composition is added to about 2 kilograms of poultry feed. 1 day-, six day- and 18 day-old chicks were placed in groups in separate isolation units equipped with feeders, water, and filtered air supply. The food and water were supplied ad libitum. For 1 day-old chicks (Table 14): Group one chicks served as the control group which received free access to diet without added bacteriocin. These chicks were challenged at day one of life with strains L4 and B1 of *C. jejuni*, as described above in Example 1. The strains were administered by oral gavages at a concentration of approximately $2 \times 10^6$ in a volume of 0.2 ml. Five of the chicks were sacrificed at about 7 days after challenge and the remaining five were sacrificed at about 10 days after challenge. Group two chicks were challenged at day 1 of life with *C. jejuni* strains L4 and B1 as described above for Group one. The chicks were given free access to diet containing approximately 250 mg of bacteriocin OR7 per kilogram of food for three days begginning from the $4^{th}$ day of life. Group two chicks were sacrificed about seven days after *C. jejuni* challenge. Group three chicks were challenged and fed as Group two chicks and sacrificed 10 days after challenge. Results are presented in Table 15.

TABLE 14

Therapeutic effects of bacteriocin OR-7 for experimentally induced *C. jejuni* infection in broilers.

| Group | Bird # | Time of Sacrifice after challenge in days | Concentration of *C. jejuni* gram/gram cecal content | Protection index in % |
|---|---|---|---|---|
| One control | 1 | 7 | 6.63 | |
| | 2 | 7 | 6.18 | |
| | 3 | 7 | 6.15 | |
| | 4 | 7 | 5.87 | |
| | 5 | 7 | 6.21 | |
| | 6 | 10 | 9.00 | |
| | 7 | 10 | 8.68 | |
| | 8 | 10 | 8.95 | |
| | 9 | 10 | 9.34 | |
| | 10 | 10 | 8.99 | |
| Two | 1 | 7 | 0.00 | 100% |
| | 2 | 7 | 0.00 | 100% |
| | 3 | 7 | 6.95 | 0.89% |
| | 4 | 7 | 0 | 100% |
| | 5 | 7 | 4.23 | 1.47% |
| | 6 | 7 | 3.25 | 1.91% |
| | 7 | 7 | 0 | 100% |
| | 8 | 7 | 0 | 100% |
| | 9 | 7 | 5.36 | 1.16% |
| | 10 | 7 | 0 | 100% |
| Three | 1 | 10 | 0 | 100% |
| | 2 | 10 | 0 | 100% |
| | 3 | 10 | 0 | 100% |
| | 4 | 10 | 0 | 100% |
| | 5 | 10 | 0 | 100% |
| | 6 | 10 | 0 | 100% |
| | 7 | 10 | 6.11 | 1.47% |
| | 8 | 10 | 0 | 100% |
| | 9 | 10 | 0 | 100% |
| | 10 | 10 | 0 | 100% |

*Therapeutic diet prepared on the basis of commercial food intended for chicks aged 1-10 days.

For 6 day-old chicks, the control groups received free access to diet without added bacteriocin. These chicks were challenged on day 2 of the experiment with approximately $10^6$ CFU in about a 0.2 ml volume) of strains L-4, and B-1 of *C. jejuni*, as described in Example 1. The *C. jejuni* was administered by oral gavages. Chicks were sacrificed 9 days, 11 days, and 14 days post challenge. Experimental chicks, having two groups, were given free access to diet with bacteriocin OR7 encapsulated in polyvinylpyrrolidone beginning from day 6 of life. These chicks were challenged on day 2 of the experiment as above for the control chicks. Chicks were sacrificed at day 9, 11, and 14 of life. Results are shown in Table 15 below.

TABLE 15

Treatment of experimental *C. jejuni*-associated infection in 6-day old chicks with bacteriocin OR7 added to feed.

| Group | Chicks per group | Time of *C. jejuni* challenge and dose in CFU | Duration of feeding days | Age of sacrificed chicks | Concentration of *C. jejuni* per gram of cecal material |
|---|---|---|---|---|---|
| Control | 4 | 2nd day $10^6$ CFU | — | 4 | $8 \times 10^8$ |
|  | 5 | 2nd day $10^6$ CFU | — | 9 | $1.8 \times 10^8$ |
|  | 5 | 2nd Day $10^6$ CFU | — | 11 | $1.02 \times 10^9$ |
|  | 5 | 2nd Day $10^6$ CFU | — | 14 | $8.2 \times 10^8$ |
| Bacteriocin* OR7 in Feed | 10 | 2nd Day $10^6$ CFU | 3 | 9 | 3 CHICKS = 0<br>1 CHICK = $1 \times 10^1$<br>4 CHICK = $1 \times 10^2$<br>2 CHICKS = $1 \times 10^3$ |
|  | 9 | 2ND Day $10^6$ CFU | 5 | 11 | 6 CHICKS = 0<br>1 CHICK01 $\times 10^1$<br>2 CHICK = $1 \times 10^4$ |
|  | 9 | 2ND Day $10^6$ CFU | 8 | 14 | 4 CHICKS = 0<br>1 CHICK = $1 \times 10^3$<br>1 CHICK = $1 \times 10^4$<br>1 CHICK = $1 \times 10^5$<br>1 CHICK = $1 \times 10^7$<br>1 CHICK = $1 \times 10^8$ |

*net dose administered to chicks for 3-day period = approximately 26.4 mg; 5-day = approximately 50.6 mg; 8-day = approximately 80.5 mg.

For 18-day old chicks, the control chicks received free access to diet without added bacteriocin. These chicks were challenged as above on day 15 of the experiment by oral gavages with a dose of $10^7$ CFU *C. jejuni* strains L-4 and B-1 in approximately a volume of 0.2 ml. Chicks were sacrificed at day 24 of the experiment. Chicks receiving conventional diet including bacteriocin OR7 as described above were given free access to feed containing approximately 0.25 g bacteriocin OR7 per kg of feed for about five days beginning on about the 19th day of life. Net therapeutic dose is about 109 mg per chick. Chicks were sacrificed on about day 24 of life. Results are shown in Table 16 below.

TABLE 16

Treatment of experimental *C. jejuni*-associated infection in 18-day old chicks with bacteriocin OR7 added to feed.

| Group | # of Chicks | Age and Dose of *C. jejuni* challenge CFU | Age of Sacrificed Chicks | Concentration (CFU) *C. jejuni* per gram of cecal material |
|---|---|---|---|---|
| Control | 5 | 15th day 10^7 CFU | 24 | $7.84 \times 10^9$ |
| Bacteriocin OR7 Treatment | 9 | 15th day 10^7 CFU | 24 | 3 CHICKS = 0 6 CHICK = $2.4 \times 10^2$ |

Chicks were challenged at 1-day of life and Control chicks were given free access to food and water without added bacteriocin. Chicks were challenged with approximately $10^6$ CFU of a mixture of strains L4 and B1 *C. jejuni* by oral gavages the 1st day of life. Control chicks were sacrificed at day 17 of life. In experimental group I, 1-day old chicks were challenged as control chicks, given free access to feed with approximately 0.250 grams of bacteriocin OR7 per kilogram of feed starting at day 14 of life and sacrificed at about day 17 of life; and group II chicks were challenged as control chicks at day 1 of life and were given free access to feed containing approximately 0.500 grams of bacteriocin OR7 per kilogram of feed at day 14 of life; and sacrificed at day 17 of life. Results are shown below in Table 17.

TABLE 17

Treatment of experimental *C. jejuni*-associated infection in chicks with bacteriocin OR7 added to feed.

| Group | # of Chicks | Age and dose of *C. jejuni* Challenge in CFU | Concentration of *C. jejuni* per gram of cecal material at Day 17 of life |
|---|---|---|---|
| Control | 10 | 1-day old $10^6$ CFU | 2 CHICKS = $4.0 \times 10^6$ 1 CHICK = $1.9 \times 10^7$ 7 CHICKS = $0.3 \times 10^9$ |
| Treated with Feed containing 0.250 g/1 kilogram Feed | 16 | 1-day old $10^6$ CFU | 14 CHICKS = 0 1 CHICK = $1.3 \times 10^3$ 1 CHICK = $1.2 \times 10^3$ |
| Treated with Feed containing 0.500/1 kilogram Feed | 16 | 1-day old $10^6$ CFU | 13 CHICKS = 0 1 CHICK = $3.5 \times 10^3$ 1 CHICK = $0.4 \times 10^3$ |

The foregoing detailed description is for the purpose of illustration. Such detail is solely for that purpose and those skilled in the art can make variations without departing from the spirit and scope of the invention.

---

What is claimed is:

1. An isolated bacteriocin having the amino acid sequence of SEQ ID NO:4, wherein the bacteriocin is isolated from *Enterococcus faecalis* (Strain LWP21) deposited with United States Department of Agricultural, Agricultural Research Service Patent Culture Collection as Accession Number NRRL-B30645.

2. An isolated *Enterococcus faecalis* (Strain LWP21) deposited with United States Department of Agricultural, Agricultural Research Service Patent Culture Collection as Accession Number NRRL-B30645.

* * * * *